Figure 2A:
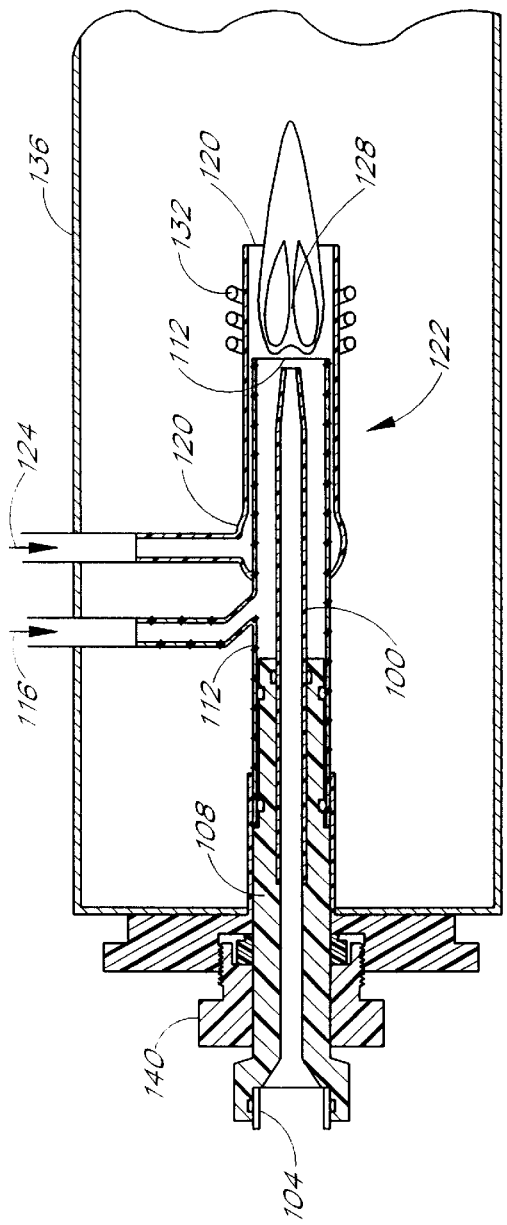

United States Patent [19]
Montaser et al.

[11] Patent Number: 6,166,379
[45] Date of Patent: Dec. 26, 2000

[54] DIRECT INJECTION HIGH EFFICIENCY NEBULIZER FOR ANALYTICAL SPECTROMETRY

[75] Inventors: Akbar Montaser, Potomac, Md.; John A. McLean, Upper Arlington, Ohio; Jerold M. Kacsir, Trabuco Canyon, Calif.

[73] Assignee: George Washington University, Washington, D.C.

[21] Appl. No.: 09/057,198

[22] Filed: Apr. 8, 1998

Related U.S. Application Data
[60] Provisional application No. 60/070,024, Dec. 30, 1997.

[51] Int. Cl.[7] .............................. H01J 49/04; G01J 3/10
[52] U.S. Cl. .................. 250/288; 356/316; 315/111.51; 219/121.5; 219/121.51; 219/121.52
[58] Field of Search ........................... 250/288; 356/316; 315/111.51; 219/121.5, 121.51, 121.52

[56] References Cited

U.S. PATENT DOCUMENTS

| | | | |
|---|---|---|---|
| 3,467,471 | 9/1969 | Greenfield et al. | 219/121 |
| 4,575,609 | 3/1986 | Fassel et al. | 219/121 PY |
| 4,989,976 | 2/1991 | Huber | 356/316 |
| 4,990,740 | 2/1991 | Meyer | 219/121.52 |
| 5,212,365 | 5/1993 | Wiederin | 219/121.52 |
| 5,867,262 | 2/1999 | Etoh et al. | 250/288 |

FOREIGN PATENT DOCUMENTS 1109602  4/1968  United Kingdom .

OTHER PUBLICATIONS

B. Sharp, "Pneumatic Nebulisers and Spray Chambers for Inductively Coupled Plasma Spectrometry: A Review, Part 1. Nebulisers", *J. Anal. At. Spectrom.*, 1988, vol. 3, pp. 613–652.

S–H. Nam et al., "High–Efficiency Nebulizer for Argon Inductively Coupled Plasma Mass Spectrometry", *J. Anal. At. Spectrom.*, 1994, vol. 9, pp. 1357–1362.

H. Liu et al., "Evaluation of a Low Sample Consumption, High–efficiency Nebulizer for Elemental Analysis of Biological Samples Using Inductively Coupled Plasma Mass Spectrometry", *J. Anal. At. Spectrom.*, 1996, vol. 11, pp. 307–311.

Liu et al., "Phase–Doppler Diagnostic Studies of Primary and Tertiary Aerosols Produced by a High–Efficiency Nebulizer", *Anal. Chem.*, 1994, vol. 66, pp. 3233–3242.

(List continued on next page.)

*Primary Examiner*—Jack Berman
*Attorney, Agent, or Firm*—Knobbe, Martens, Olson & Bear, LLP

[57] ABSTRACT

A simple, relatively low-cost direct injection high efficiency nebulizer (DIHEN) is suitable for argon inductively coupled plasma (Ar ICP) spectrometry. The DIHEN may be operated at solution uptake rates of 1–100 $\mu$L/min. Analytical performance indices for the DIHEN and fundamental characteristics of the aerosol produced are obtained using an ICP mass spectrometer (ICPMS) and a 2-dimensional phase Doppler particle analyzer (2D PDPA), respectively. Results are compared to those obtained with a conventional cross-flow pneumatic nebulizer (PN), equipped with a Scott-type spray chamber. Droplet sizes and velocities produced with the DIHEN are smaller than those reported for the direct injection nebulizer (DIN). The DIHEN offers optimal sensitivity at low injector gas flow rates (approx. 0.25 L/min) and high RF power (approx. 1.5 kW). For the 17 elements tested, detection limits (ppt) and sensitivities achieved with the DIHEN (at 85 $\mu$L/min) are similar to or better than those obtained on the same instrument using the PN (at 1 mL/min). However, because the primary aerosol is injected directly into the plasma, oxide-to-metal ion ratios ($MO^+/M^+$) are high as in the case of the DIN. The utility of the DIHEN for the analysis of small volume samples is demonstrated by microscale flow injection analysis ($\mu$FIA) of Cr bound to human lung DNA. Detection of Cr at the femtogram level is feasible.

21 Claims, 17 Drawing Sheets

OTHER PUBLICATIONS

Liu et al., "Investigation of a high–efficiency nebulizer and a thimble glass frit nebulizer for elemental analysis of biological materials by inductively coupled plasma–atomic emission spectrometry", *Spectrochim. Acta* 1996, vol. 51B, pp. 27–40.

Olesik et al., "Inductively Coupled Plasma Optical Emission Spectrometry Using Nebulizers with Widely Different Sample Consumption Rates", *Anal. Chem.*, 1994, vol. 66, pp. 2022–2030.

Pergantis et al., "Microscale Flow Injection and Microbore High–Performance Liquid Chromatography Coupled with Inductively Coupled Plasma Mass Spectrometry via High–Efficiency Nebulizer", *Anal. Chem.*, 1995, vol. 67, pp. 4530–4535.

Vanhaecke et al., "Evaluation of a Commercially Available Microconcentric Nebulizer for Inductively Coupled Plasma mass Spectrometry", *J. Anal. At. Spectrom.*, 1996, vol. 11, pp. 543–548.

Augagneur et al., "Determination of Rare Earth Elements in Wine by Inductively Coupled Plasma Mass Spectrometry Using a Microconcentric Nebulizer", *J. Anal. At. Spectrom.*, 1996, vol. 11, pp. 713–721.

Lawrence et al., "Direct Liquid Sample Introduction for Flow Injection Analysis and Liquid Chromatography with Inductively Coupled Argon Plasma Spectrometric Detection", *Anal. Chem.*, 1984, vol. 56, pp. 289–292.

LaFreniere et al., "Flow Injection Analysis with Inductively Coupled Plasma–atomic Emission Spectroscopy: Critical Comparison of Conventional Pneumatic, Ultrasonic and Direct Injection Nebulization", *Spectrochim. Acta* 1985, vol. 40B, pp. 1495–1504.

LaFreniere et al., "Elemental Speciation via High–Performance Liquid Chromatography Combined with Inductively Coupled Plasma Atomic Emission Spectroscopic Detection: Application of a Direct Injection Nebulizer", *Anal. Chem.*, 1987, vol. 59, pp. 879–887.

Avery et al., "Characterization and Optimization of a Direct Injection Nebulizer for Introduction of Organic Solvents and Volatile Analyte Species into a Inductively Coupled Plasma", *Appl. Spectrosc.*, 1990, vol. 44, pp. 1690–1698.

Wiederin et al., "Direct Injection Nebulization for Inductively Coupled Plasma Mass Spectrometry", *Anal. Chem.*, 1991, vol. 63, pp. 219–225.

Wiederin et al., "On–Line Standard Additions with Direct Injection Nebulization for Inductively Coupled Plasma Mass Spectrometry", *Anal. Chem.*, 1991, vol. 63, pp. 1626–1631.

Smith et al., "Measurement of boron concentration and isotope ratios in biological samples by inductively coupled plasma mass spectrometry with direct injection nebulization", *Analytica Chimica Acta*, 1991, vol. 248, pp. 229–234.

Shum et al., "Speciation of Mercury and Lead Compounds by Microbore Column Liquid Chromatography—Inductively Coupled Plasma Mass Spectrometry with Direct Injection Nebulization", *Anal. Chem.*, 1992, vol. 64, pp. 2444–2450.

Shum et al., "Elemental Speciation by Liquid Chromatography—Inductively Coupled Plasma Mass Spectrometry With Direct Injection Nebulization", *Analyst.* 1992, vol. 117, pp. 577–582.

Powell et al., "Inductively Coupled Plasma Mass Spectrometry with Direct Injection Nebulization for Mercury Analysis of Drinking Water", *Anal. Chem.*, 1992, vol. 64, pp. 2253–2257.

Shum et al., "Elemental Speciation by Anion Exchange and Size Exclusion Chromatography with Detection by Inductively Coupled Plasma Mass Spectrometry with Direct Injection Nebulization", *Anal. Chem.*, 1993, vol. 65, pp. 2972–2976.

Powell et al., "Determination of Chromium Species in Environmental Samples Using High–Pressure Liquid Chromatography Direct Injection Nebulization and Inductively Coupled Plasma Mass Spectrometry", *Anal. Chem.*, 1995, vol. 67, pp. 2474–2478.

Zoorob et al., "Evaluation of the Direct Injection Nebulizer in the Coupling of High–Performance Liquid Chromatography to Inductively Coupled Plasma Mass Spectrometry", *J. Anal. At. Spectrom.*, 1995, vol. 10, pp. 853–858.

Liu et al., "Capillary Electrophoresis Coupled On–Line with Inductively Coupled Plasma Mass Spectrometry for Elemental Speciation", *Anal. Chem.*, 1995, vol. 67, pp. 2020–2025.

Wiederin et al., "Measurement of Aerosol Particle Sizes from a Direct Injection Nebulizer", *Appl. Spectrosc.*, 1991, vol. 45, pp. 1408–1412.

Shum et al., "Spatially Resolved Measurements of Size and Velocity Distributions of Aerosol Droplets from a Direct Injection Nebulizer", *App. Spectrosc.*, 1993, vol. 47, pp. 575–583.

Christodoulou et al., "Determination of Gold and Platinum in the Presence of Blood Plasma Proteins Using Inductively Coupled Plasma Mass Spectrometry with Direct Injection Nebulization", *J. Anal. At. Spectrom.*, 1996, vol. 11, pp. 1031–1035.

French et al., "Monodisperse Dried Microparticulate Injector for Analytical Instrumentation", *Anal. Chem.*, 1994 vol. 66, pp. 685–691.

Olesik et al., "Monodisperse Dried Microparticulate Injector: A New Tool for Studying Fundamental Processes in Inductively Coupled Plasmas", *Anal. Chem.*, 1994, vol. 66, pp. 3371–3378.

Dziewatkoski et al., "Time–Resolved Inductively Coupled Plasma Mass Spectrometry Measurements with Individual, Monodisperse Drop Sample Introduction", *Anal. Chem.*, 1996, vol. 68, pp. 1101–1109.

Allen et al., "Spatial Location of the Space Charge Effect in Individual Ion Clouds Using Monodisperse Dried Microparticulate Injection with a Twin Quadrupole Inductively Coupled Plasma Mass Spectrometer", *Anal. Chem.*, 1997, vol. 69, pp. 2384–2391.

Olesik, "Investigating the Fate of Individual Sample Droplets in Inductively Coupled Plasmas", *Appl. Spectrosc.* 1997, vol. 51, pp. 158A–175A.

Olesik et al., "Observation of Atom and Ion Clouds Produced From Single Droplets of Sample in Inductively Coupled Plasmas by Optical Emission and Laser–Induced Fluorescence Imaging", *Appl. Spectrosc.*, 1997, vol. 51, pp. 607–616.

Lazar et al., "Investigation of the Analytical Performance of an MDMI–ICP–AES System", *Appl. Spectrosc.*, 1997, vol. 51, pp. 617–624.

Montaser et al., "Argon Inductively Coupled Plasma Mass Spectrometry with Thermospray, Ultrasonic, and Pneumatic Nebulization", *Anal. Chem.*, 1991, vol. 63, pp. 2660–2665.

Clifford et al., "Diagnostic Studies on Desolvated Aerosols from Ultrasonic Nebulizers", *Spectrochim. Acta,* 1992, vol. 47B, pp. 1107–1122.

McLean et al., "A Direct Injection High Efficiency Nebulizer for Inductively Coupled Plasma Mass Spectrometries", Pittcon Conference, Mar. 1997, Atlanta, GA. (oral presentation).

McLean et al., "Fundamental Investigation of a Direct Injection High Efficiency Nebulizer for Inductively Coupled Plasma Mass Spectrometry", FACSS Conference, Oct. 1997, Providence, Rhode Island. (oral presentation).

JE Meinhard Associates Inc., Brochure, Ca. 1993.

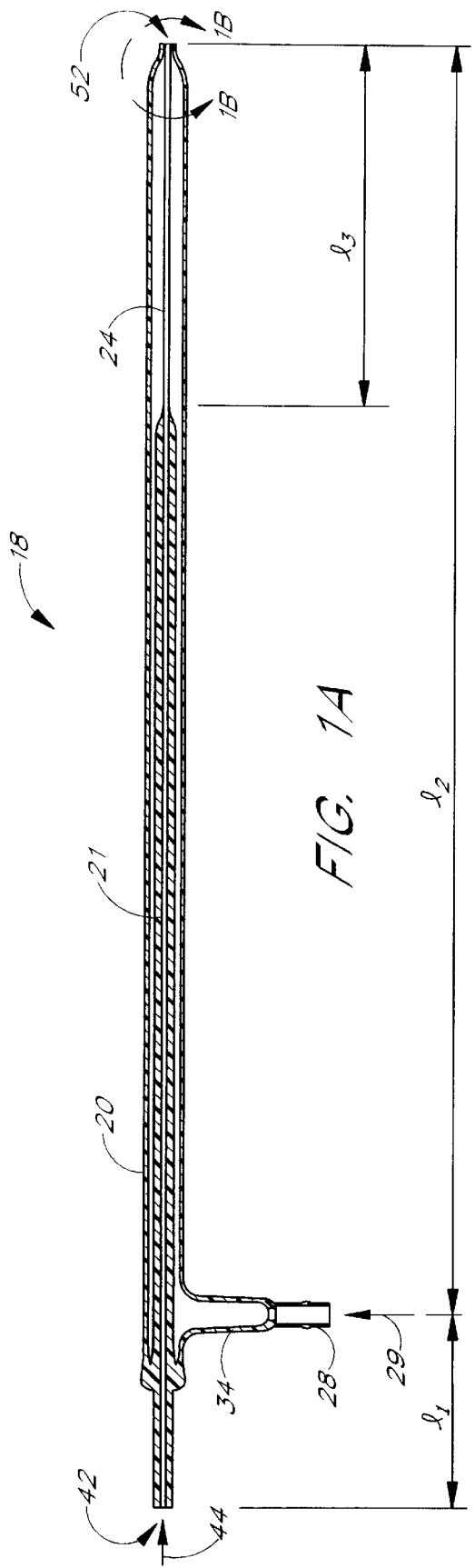
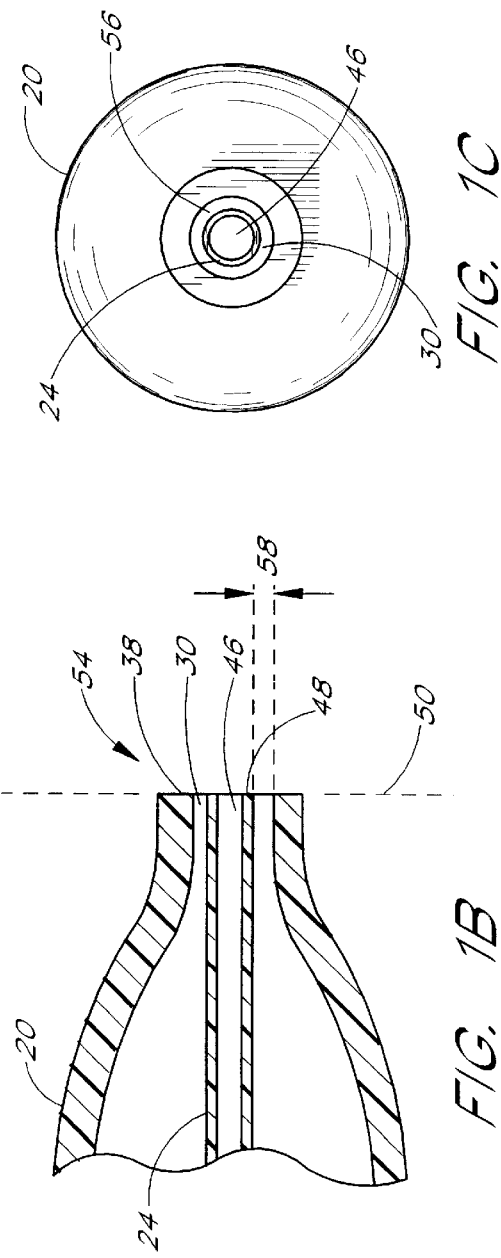

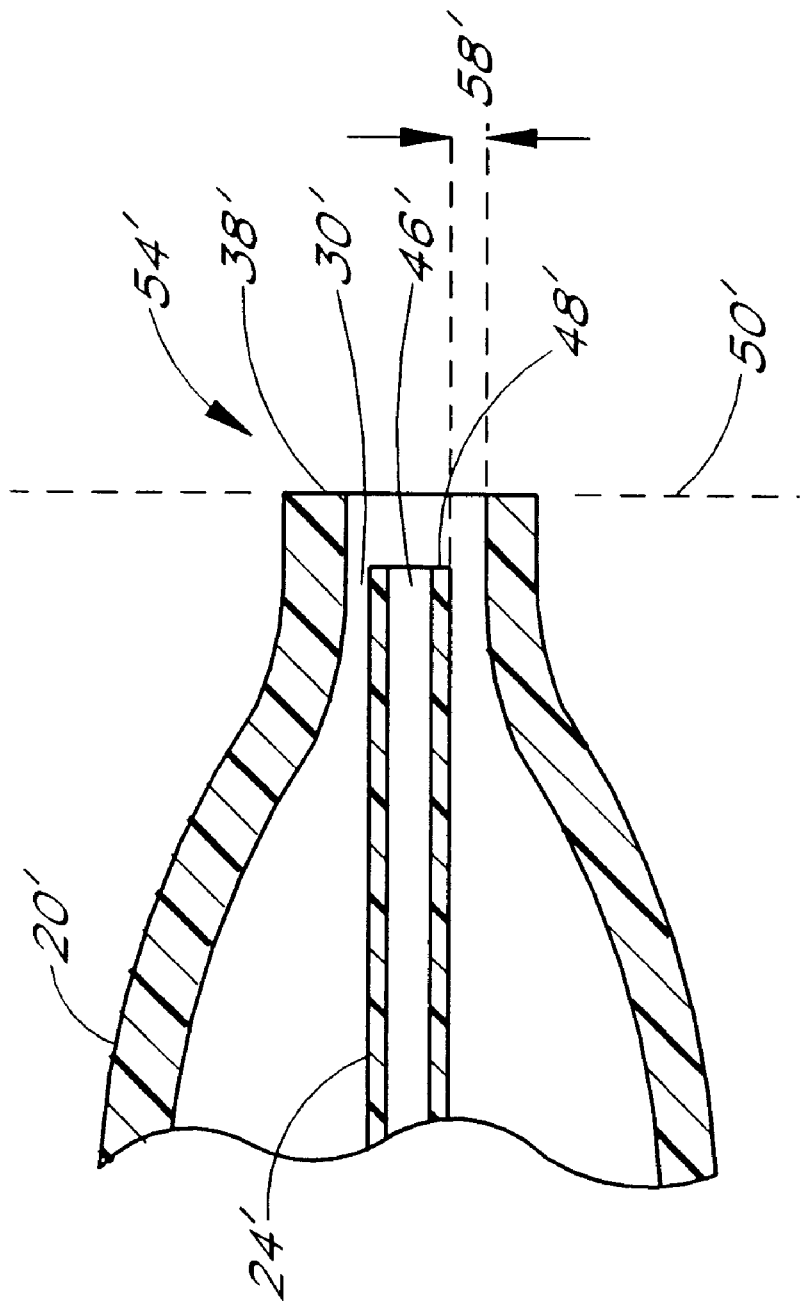

Figure 6A:
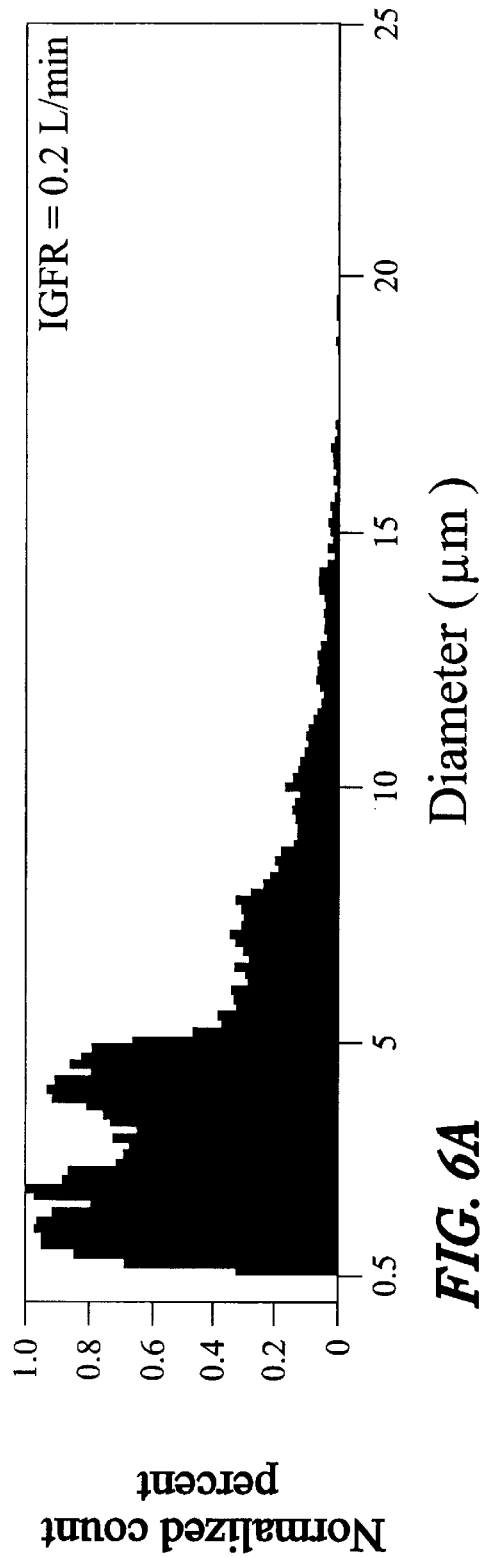
Figure 6B:
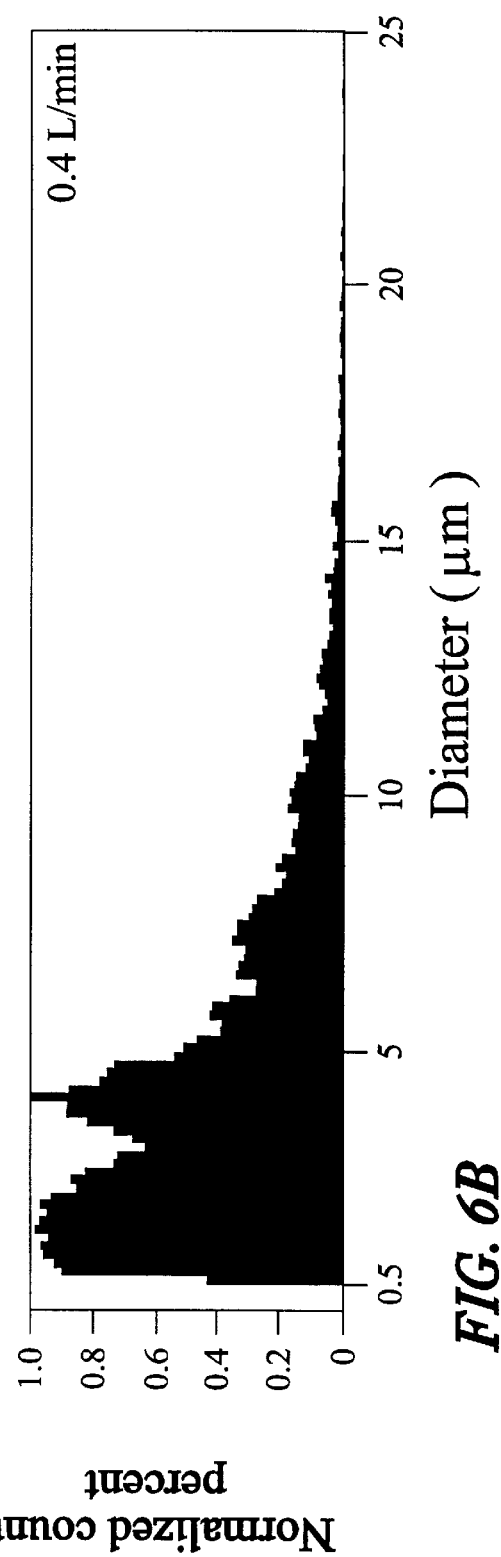
Figure 7A:
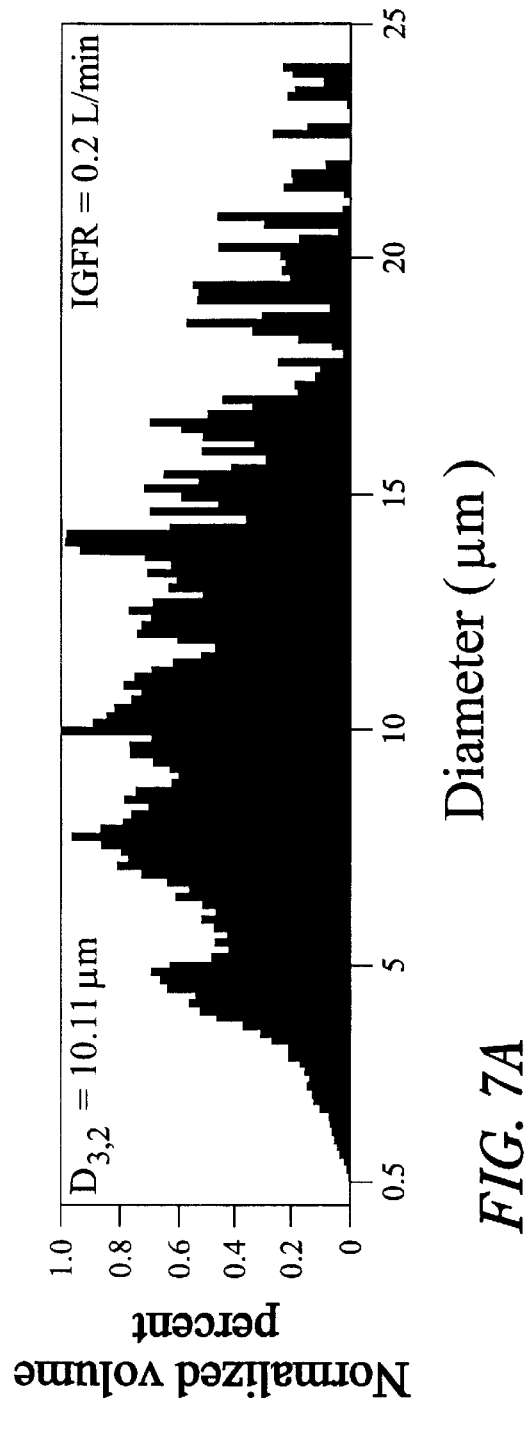
Figure 7B:
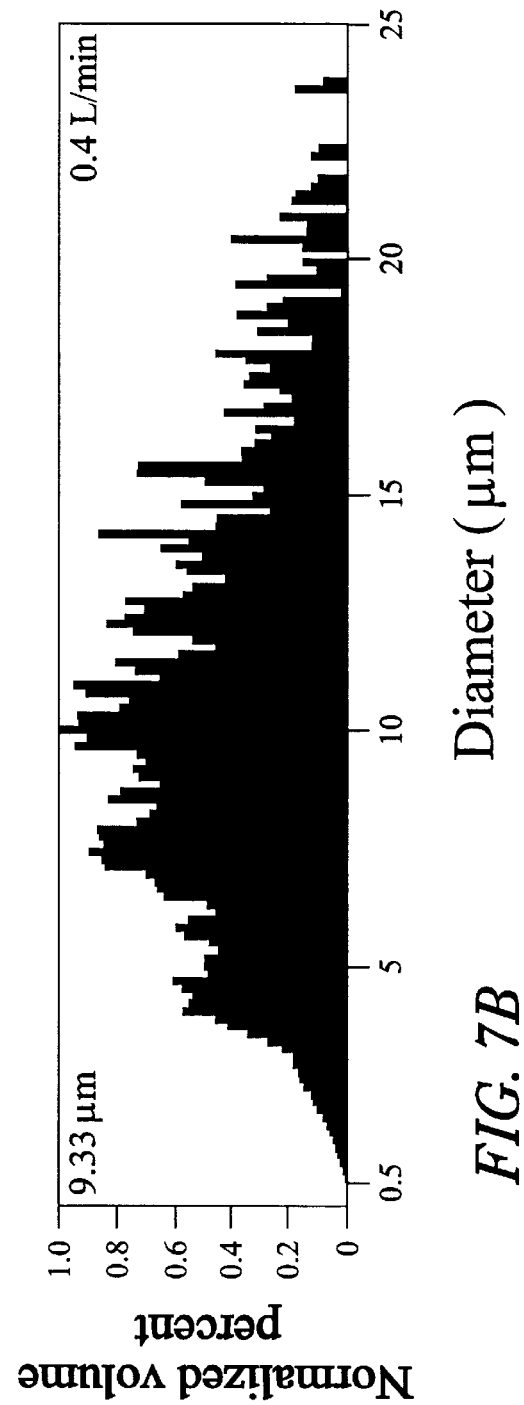
Figure 7C:
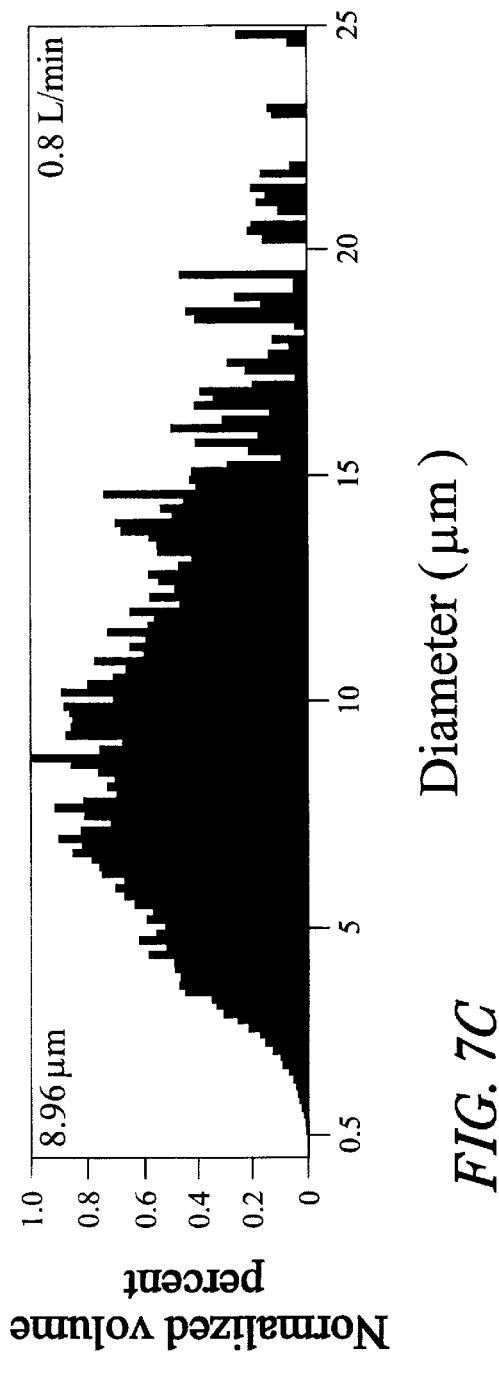
Figure 7D:
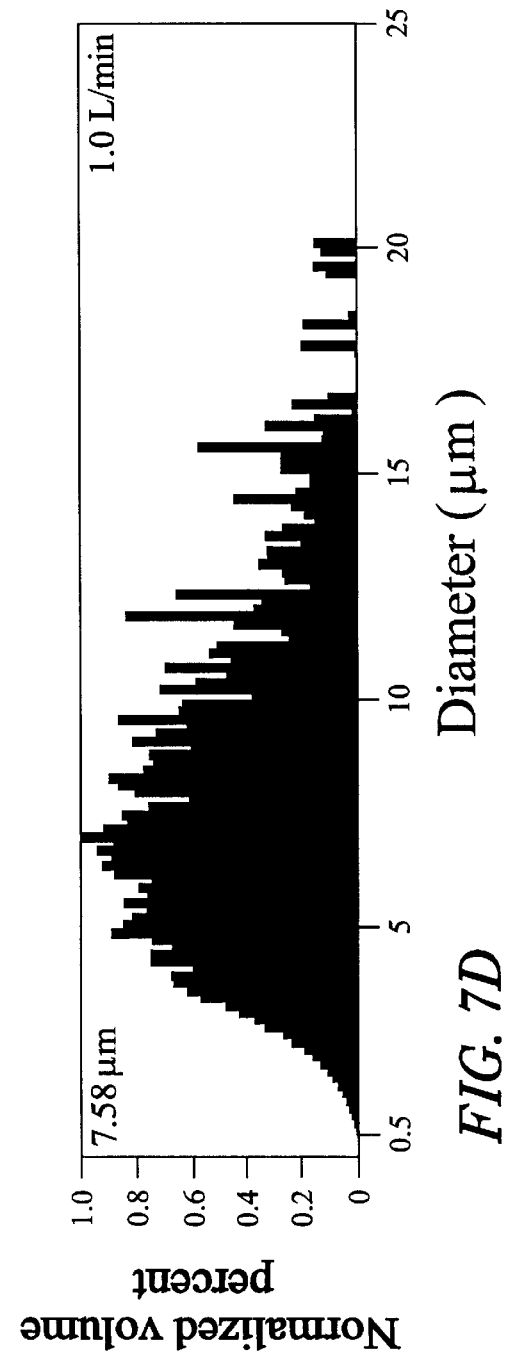
Figure 8A:
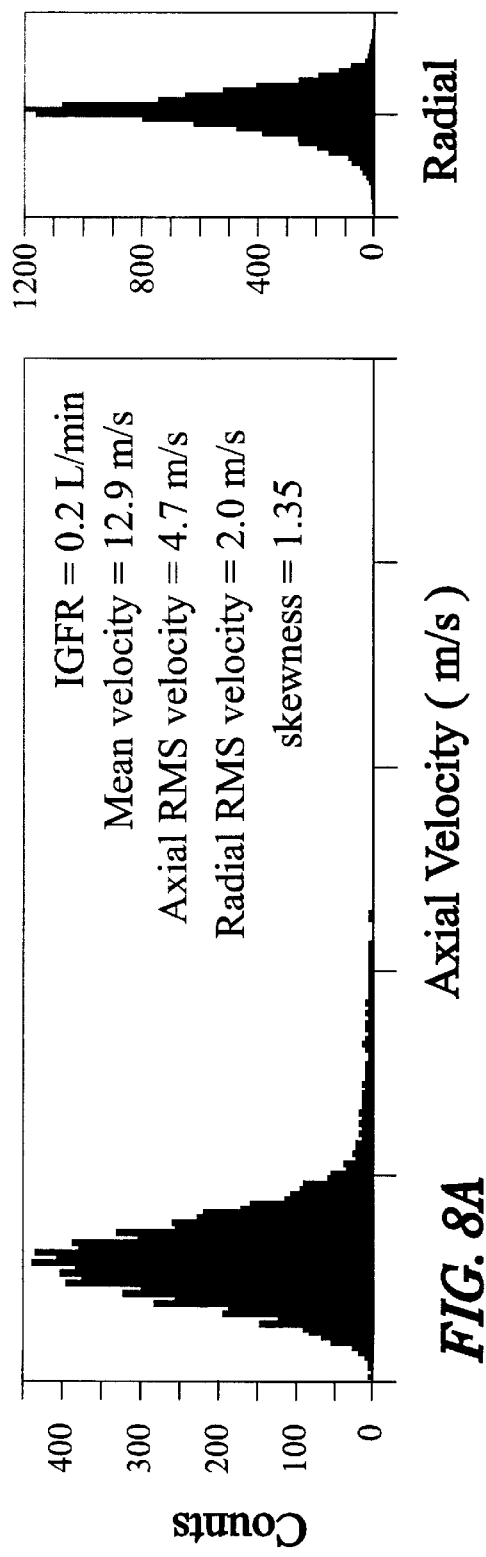
Figure 8B:
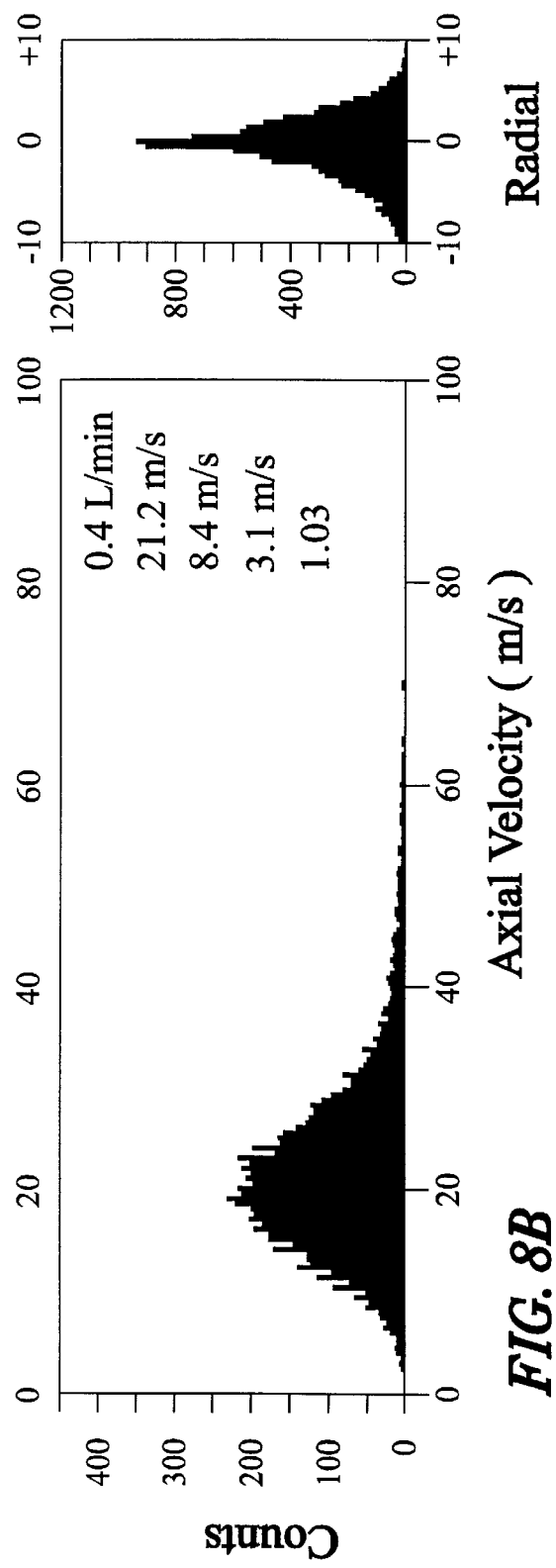
Figure 8C:
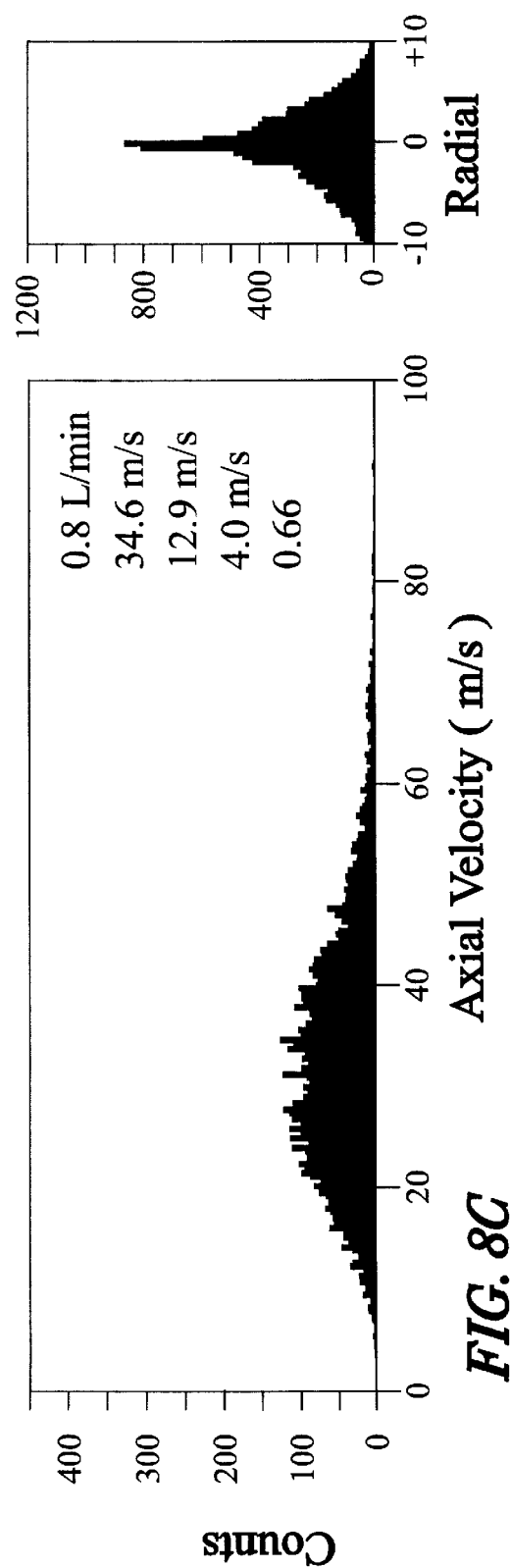
Figure 8D:
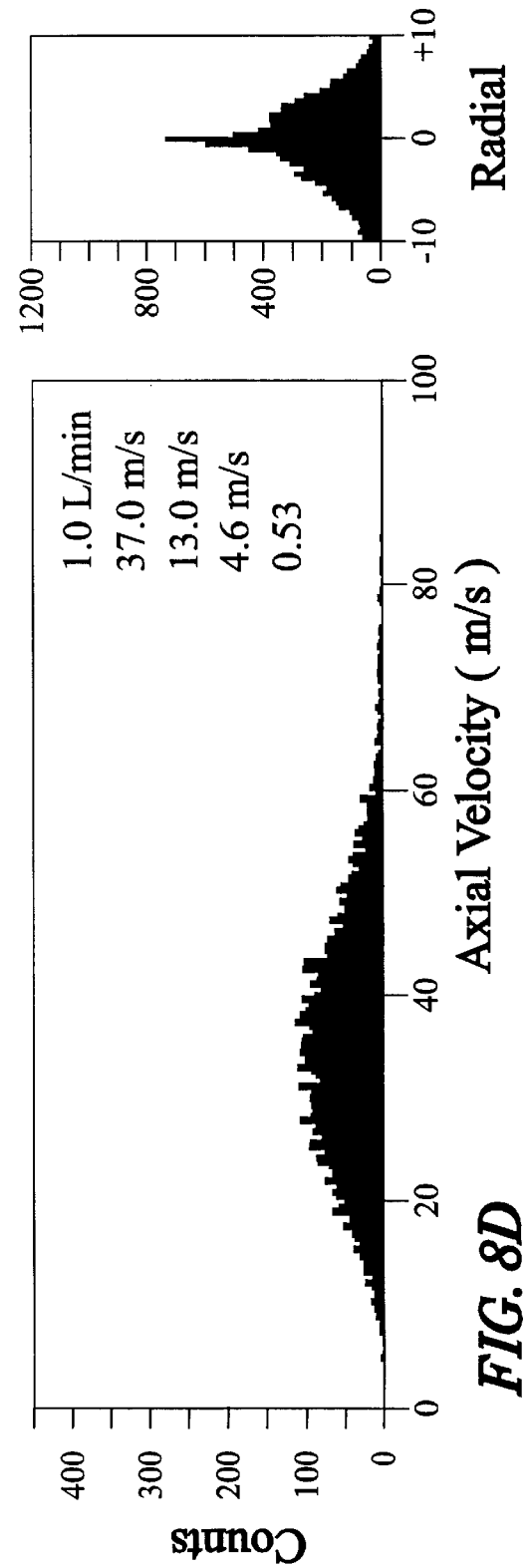

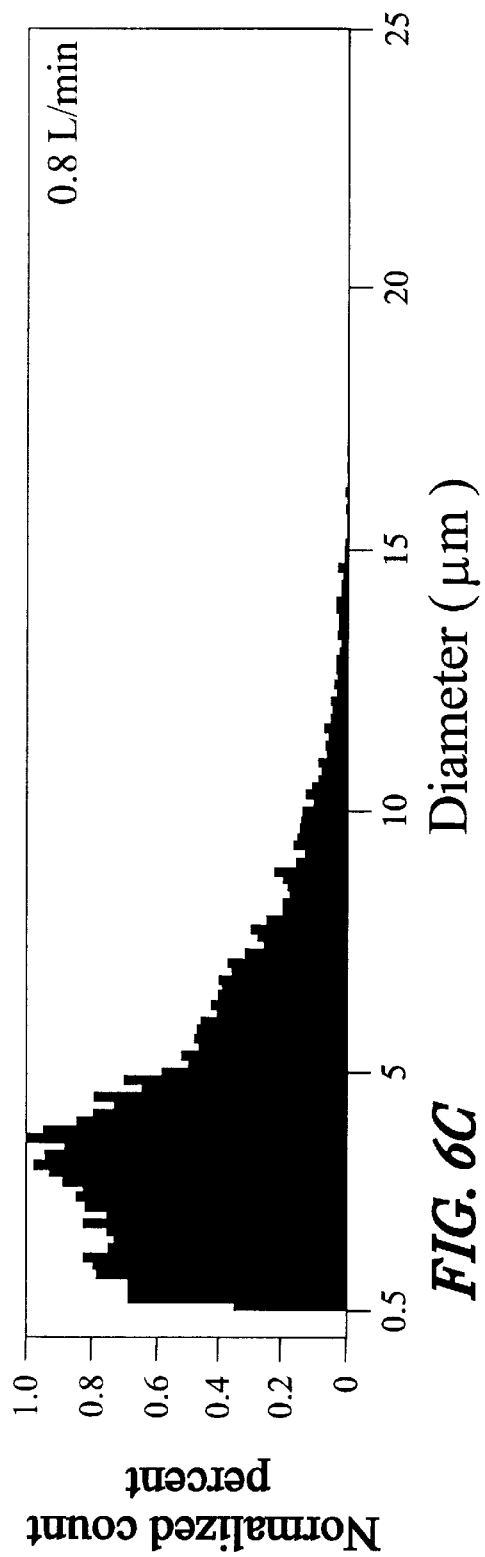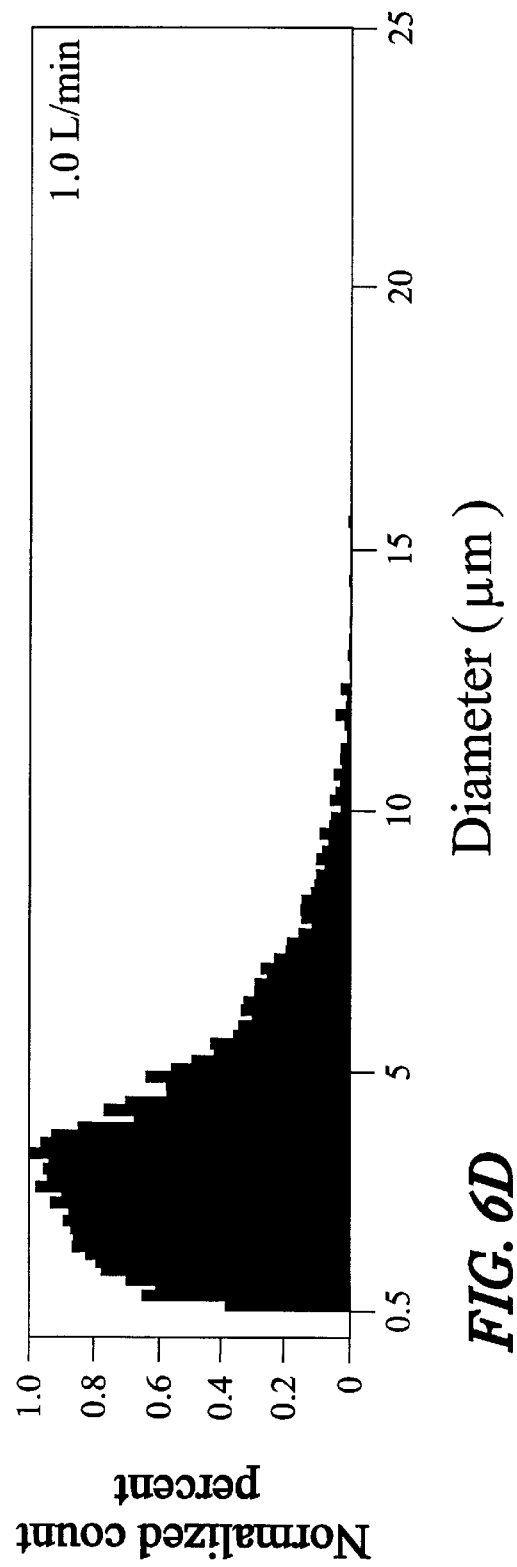
FIG. 6C
FIG. 6D

DIRECT INJECTION HIGH EFFICIENCY NEBULIZER FOR ANALYTICAL SPECTROMETRY

RELATED APPLICATIONS

The present application claims priority from U.S. Provisional Application Ser. No. 60/070,024 filed on Dec. 30, 1997.

BACKGROUND OF THE INVENTION

1. Field of the Invention

The present invention relates generally to nebulizers for use in analytical spectrometry such as inductively coupled mass spectrometry, and more generally to direct injection nebulizers.

2. Description of the Related Art

In inductively coupled plasma (ICP) spectrometries, test solutions are typically introduced into the plasma in the form of an aerosol. The combination of a pneumatic nebulizer (PN) with a spray chamber is primarily used in ICP spectrometries because of its simplicity and low cost. However, this arrangement suffers from low analyte transport efficiency (typically 1–2%) and high sample consumption (typically 1–2 mL/min). A simple, low-consumption, highly efficient nebulizer is often required in chromatographic applications and also for the direct analysis of semiconductor, biological, forensic, or toxic materials. In these and other cases, the sample is limited, expensive, or hazardous, and it may contain a large fraction of organic solvents that can substantially alter the plasma characteristics. Presently available microflow nebulizers include pneumatic devices such as the high-efficiency nebulizer (HEN), the microconcentric nebulizer (MCN), the direct injection nebulizer (DIN), and the oscillating capillary nebulizer (OCN), as well as piezoelectrically driven devices such as the microflow ultrasonic nebulizer ($\mu$-USN) and the monodisperse dried microparticulate injector (MDMI). Among these devices, the DIN has received significant attention, partly because in this device the nebulizer is an integral part of the ICP torch, and thus 100% of the aerosol is presented to the plasma. This attribute along with the low internal dead volume (<2 $\mu$L) of the DIN leads to several other benefits, namely: low memory effects, rapid response times, and good precision. These characteristics are particularly important for interfacing liquid chromatography equipment to ICP-based instruments.

Unfortunately, the setup required for the DIN is more expensive and complex than the conventional pneumatic nebulizer-spray chamber arrangement. The DIN also requires a high pressure pump for sample delivery. Further, because no spray chamber is used, relatively large, high-velocity droplets with broad size-velocity distributions are introduced into the plasma. These drawbacks result in reduced sensitivity, impaired precision, and increased matrix effects.

The HEN-spray chamber combination offers detection limits (ppt) at solution uptake rates of less than 100 $\mu$L/min (similar to conventional PNs operated at 1–2 mL/min), and the primary aerosol produced by the HEN exhibits droplet-size distributions that are smaller and narrower than those reported for the DIN (see S. C. K. Shum, S. K. Johnson, H-M. Pang, and R. S. Houk, "Spatially Resolved Measurements of Size and Velocity Distributions of Aerosol Droplets from a Direct Injection Nebulizer," Applied Spectroscopy, vol. 47, pp. 575–583, 1993). However, the HEN is configured to be used with a spray chamber, and does not permit direct injection of the aerosol into the plasma.

Accordingly, there is a need for a simple, low-cost device that produces relatively small droplet sizes in a relatively narrow droplet size distribution for direct injection of microliter quantities of test solutions into the plasma.

SUMMARY OF THE INVENTION

The direct injection high efficiency nebulizer disclosed herein offers detection limits (ppt) with Ar Inductively Coupled Plasma Mass Spectrometry (ICPMS) at 85 $\mu$L/min that are similar to, or better than, a conventional crossflow PN using a spray chamber at 1 mL/min. This represents at least a 12-fold improvement in the absolute detection limits. Additionally, both sensitivity and precision are generally improved over the conventional PN. Compared with the DIN, the Direct Injection High-Efficiency Nebulizer (DIHEN) disclosed herein is simple, easy to use, and relatively inexpensive. Importantly, the DIHEN does not require a high pressure pump for its operation. Because the test solution is nebulized directly into the plasma, polyatomic species are present to a greater extent compared with conventional nebulization, similar to behavior found for the DIN. When used in the $\mu$FI mode, peak-to-peak precision is on the order of 2% RSD (N=10), and femtogram detection limits are obtained in the determination of Cr bound to DNA samples. Although the results disclosed herein are concerned with ICPMS, the DIHEN may be used as a micronebulizer in other plasma-based technologies.

In one preferred embodiment of the invention, the direct injection high efficiency nebulizer includes an elongate tubular shell having a gas input port and a gas output port. The nebulizer also includes a capillary tube within the tubular shell, in which the capillary tube has a sample input port and a sample output port. The shell has a terminus at the gas output port, and the capillary tube has a terminus at the sample output port, in which the capillary tube terminus is substantially at or proximal to the shell terminus. Each of the input ports are separated from both of the output ports by at least 10 cm, so that the nebulizer is insertable in a torch for direct injection of aerosol towards an interaction region, e.g., a plasma interaction region. The shell and the capillary tube form a nozzle having an annular region between the shell and the capillary tube. When gas pressure is applied to the gas input port, the gas flows through the nebulizer and out of the nozzle. The size of the annular region is selected so that a gas flow rate through the nozzle of 1 liter/min is achievable using argon gas at a pressure in a range of 20 to 300 psi.

Another aspect of the invention comprises a method of aerosol production and injection which includes the steps of outputting gas from a gas output port of a nebulizer, outputting a sample from a sample output port of the nebulizer (in which the sample output port is substantially at or proximal to the gas output port, and the gas nebulizes the sample to produce an aerosol), and positioning the nebulizer so that the aerosol is injected towards a plasma interaction region. In a preferred embodiment, the sample is a liquid, and the plasma interaction region includes a flame or an inductively coupled plasma.

Yet another aspect of the invention comprises a direct injection high efficiency nebulizer which includes an elongate tubular shell having a gas input port and a gas output port. The nebulizer also includes a capillary tube within the tubular shell, in which the capillary tube has a sample input port and a sample output port. Each of the input ports is separated from both of the output ports by at least 10 cm, whereby the nebulizer is insertable in a torch for direct injection of aerosol towards an interaction region.

BRIEF DESCRIPTION OF THE DRAWINGS

FIG. 1A is a schematic diagram of a preferred embodiment of the Direct Injection High Efficiency Nebulizer (DIHEN).

FIG. 1B is a longitudinal cross sectional view of the tip of the nebulizer shown in FIG. 1A.

FIG. 1C is an end view of the tip of the nebulizer shown in FIGS. 1A and 1B.

FIG. 1D is a longitudinal cross sectional view of the tip of a DIHEN nebulizer in which the capillary tube is slightly recessed with respect to the shell.

FIG. 2A is a schematic of a typical torch box setup for use in inductively coupled mass spectrometry.

FIG. 2B is a schematic of a setup similar to that of FIG. 2A, in which the DIHEN of FIGS. 1A, 1B, and 1C is used.

FIGS. 2C and 2D show critical dimensions of the DIHEN Delrin® demountable torch adapter used in the setup of FIG. 2B.

FIG. 3A shows normalized signal intensity as a function of RF power when the DIHEN is operated with an injector gas flow rate of 0.25 L/min and a solution uptake rate of 11 $\mu$L/min.

FIG. 3B shows sensitivity as a function of injector gas flow rate when the DIHEN is operated at a solution uptake rate of 11 $\mu$L/min and the RF power is 1500 W.

FIG. 4 shows sensitivity as a function of solution uptake rate for the DIHEN when operated at an injector gas flow rate of 0.25 L/min.

FIGS. 5A and 5B show normalized signal intensity and ion intensity ratios for oxides and doubly charged species as a function of the injector gas flow rate for a solution uptake rate of 11 $\mu$L/min and RF power of 1500 W.

FIGS. 6A–D and FIGS. 7A–D show droplet size distributions in normalized count and volume percent, respectively, as a function of injector gas flow rate, in which each distribution represents approximately 10,000 droplets. The water aerosol produced by the DIHEN was probed at a position 15 mm from the nozzle along the centerline of the aerosol cone, and the solution uptake rate was 85 $\mu$L/min.

FIGS. 8A–D show the variation of axial and radial droplet velocity distributions with injector gas flow rates for the experimental conditions of FIGS. 6A–D and 7A–D, in which positive radial velocity is defined as the velocity component perpendicular to the centerline of the aerosol in the vertical direction.

FIG. 9 shows a block diagram of the injection system used in the DIHEN-ICPMS microscale flow injection analysis experiments.

FIG. 10 shows peak-profiles for 10 repeat injections of 10 ppb Cr via a 20 $\mu$L sample loop. The solid-line represents the response monitored at m/z 53, while the dotted-line represents the response monitored at m/z 50. Carrier solvent was introduced at 85 $\mu$L/min, and the DIHEN was operated with an injection gas flow rate of 0.25 L/min.

FIG. 11 shows peak-profiles for six repeat injections of Cr-DNA. The first 3 peaks are a 1 to 1 dilution of Cr-DNA and 2% $UNO_3$, while the second 3 peaks are a 1 to 1 dilution of Cr-DNA with 10 ppb Cr in 2% $HNO_3$ yielding a 5 ppb matrix matched standard addition.

DETAILED DESCRIPTION OF THE PREFERRED EMBODIMENT

The Direct Injection High Efficiency Nebulizer. The device disclosed herein is referred to as a Direct Injection HEN (DIHEN). A schematic diagram of one embodiment of the DIHEN (J. E. Meinhard Associates, Inc., Santa Ana, Calif., USA) is shown in FIGS. 1A, 1B, and 1C. The DIHEN 18 is preferably constructed from borosilicate glass and includes an elongate tubular shell 20 around a capillary tube 24. The shell 20 may be formed from 6 mm O.D. tubing and includes a gas input port 28 (for accepting injector gas 29) and a gas output port 30. The thick wall 21 of the proximal portion of the capillary tube 24 enhances the robustness of the DIHEN 18 and reduces the possibility of damage to the capillary tube 24 due to resonance oscillations arising from the injector gas 29. Microscopic inspection of the distal end of the DIHEN 18 and the capillary tube 24 showed no visible signs of damage after approximately 150 hours of operation.

The gas input port 28 is preferably located within a sidearm 34 of the DIHEN 18, whereas the gas output port 30 is located at a terminus 38 of the shell 20. The capillary tube 24 includes a sample input port 42 through which a sample 44 to be analyzed (preferably a liquid) is injected, as well as a sample output port 46 located at a terminus 48 of the capillary tube 24. The terminus 48 of the capillary tube 24 and the terminus 38 of the shell 20 preferably lie in a common plane 50 to define a nozzle 52 having an end surface 54. In the embodiment shown, the gas output port 30 is formed by an annular region 56 between the capillary tube 24 and the shell 20 at the nozzle 52. While it is preferred that the ends of the capillary tube 24 and shell 20 be coterminous, the capillary tube may be recessed slightly (up to 0.030") with respect to the shell, as illustrated in FIG. 1D, in which the primed numerals designate parts analogous to their unprimed counterparts of FIG. 1B. Unlike the DIN (see, for example, "Direct Liquid Sample Introduction for Flow Injection Analysis and Liquid Chromatography with Inductively Coupled Argon Plasma Spectrometric Detection," K. E. Lawrence et al., Analytical Chemistry, vol. 56, pp. 292–293, 1984), the DIHEN 18 requires no auxiliary nebulizer gas passageway. In one preferred embodiment of the invention (see FIG. 1A), the capillary tube 24 tapers down over a length ($l_3$) of about 48 mm towards its terminus 48 where the capillary tube has the following dimensions: an inside diameter (I.D.) of 82 $\mu$m, a wall thickness of 35 $\mu$m, and an annular region 56 of 0.0099 $mm^2$, corresponding to an annular gap 58 of about 18.5 $\mu$m. As used herein, the term "annular gap" means the radial dimension between the outer surface of the capillary tube 24 and the inner surface of the shell 20 at the annular region 56. In this preferred embodiment, at distances greater than about 48 mm from the terminus 48 of the capillary tube 24, the capillary tube flares out to an outside diameter (O.D.) of ⅛." The shell 20 and the capillary tube 24 preferably join each other at that end of the DIHEN 18 that includes the sample input port 42. In the embodiment shown in FIG. 1A, the sidearm 34 is separated from the nozzle 52 and the sample input port 42 by about 175 mm ($l_2$) and 33 mm ($l_1$), respectively. The DIHEN 18 dead volume may preferably be on the order of approximately 55 $\mu$L or less. In general, each of the input ports 28 and 42 are preferably separated from the output ports 30 and 46 by at least 10 cm, and the nozzle 52 is preferably located just before the base of the plasma, as illustrated below in connection with FIG. 2B.

The shell 20 and the capillary tube 24 both taper down at that end of the DIHEN 18 that includes the nozzle 52. The sample 44 is drawn out of the capillary tube 24 by the Venturi effect caused by the injector gas 29 flowing out of the gas output port 30, whereupon the sample 44 breaks up to form an aerosol which can be analyzed, as discussed below in connection with FIG. 2B. Alternatively, a pump (e.g., peristaltic, syringe, gas displacement, or high performance liquid chromatography (HPLC) pump) may be used to supplement the Venturi effect and thereby increase the flow rate of the sample. Thus, the cross sectional area of the annular region 56 and the size of the annular gap 58 are important parameters in the design of the DIHEN 18. Suitable flow characteristics may be obtained utilizing as a starting material glassware in which the shell 20 and the capillary tube 24 taper down such that they are fused together at their distal end, i.e. they have no annular gap 58 at the distal end. The glassware may then be lapped or polished down until a suitable annular region 56 and annular gap 58 have been defined. One preferred method is to alternately lap down the glassware and test it by injecting argon gas through the sidearm 34 with the sample input port 42 blocked, while monitoring both the gas pressure at the sidearm and the gas flow rate. For example, satisfactory results may be obtained when a gas flow rate of 1 liter/min is obtained for an argon gas pressure at the sidearm 34 that is between 20 and 300 psi, or alternatively, for an argon gas pressure of 60–275 psi or 160–180 psi. By way of example, the inside diameter of the capillary tube 24 may be between 50 to 150 microns (preferably less than about 175 microns), and the annular gap 58 may be on the order of 20 microns, and more generally in the range of 1–100 microns.

In determining the figures of merit for the DIHEN 18 (discussed in connection with Table 2 below), solutions were introduced into the DIHEN 18 in a continuous flow mode. For this purpose, a syringe pump was used for flow rates between 5–42 $\mu$L/min, whereas for solution flow rates of 85 $\mu$L/min, a 4-channel peristaltic pump was used. In contrast to the DIN, the DIHEN 18 does not require a high pressure pump for sample delivery. Narrow bore tygon tubing (0.015" i.d.) was utilized for faster switching of test solutions. The pumps and their relationship with the DIHEN 18 are discussed below in connection with FIG. 9.

The flow rate of the injector gas 29 (preferably argon, although other gases can be used, especially the rare or noble gases) into the sidearm 34 was controlled by a mass flow controller, which is not shown in the figures. To maintain an argon flow rate of 0.25 L/min, a back pressure of approximately 52 psig was required. The back pressure to the mass flow controller was maintained at 180 psig to allow variation of the injector gas flow rate from 0.2 to 1.0 L/min.

The Ar ICPMS Instrument. Analytical characteristics of the DIHEN 18 were investigated using an Elan 6000 ICPMS system (Perkin-Elmer/Sciex Corporation, Norwalk, Conn., USA) under the operating conditions listed in Table 1. All analytical data were collected under standard laboratory conditions, i.e., not in a clean-room environment. Data were collected in the peak hopping mode with a dwell time of 20 ms, and an integration time of 1 s/mass. The lens voltage was auto-optimized for each n/z.

The results described herein were obtained with two nebulization systems, and these results are compared against each other and with results obtained with the HEN system described by S- H. Nam et al. (J. Anal. At. Spectr., vol. 9, pp. 1357–1362, 1994). The torch box setup for the first system is shown in FIG. 2A and is used with a conventional cross flow pneumatic nebulizer (Model GemTip, Perkin-Elmer Corporation, Norwalk, Conn., USA) and a Ryton Scott-type spray chamber having an internal volume of 97 mL, which are not shown in the figures. A demountable torch adapter 108 mates with a torch injector 100. An inner torch tube 112 (preferably quartz) through which auxiliary gas 116 is supplied surrounds the torch injector 100. The inner torch tube 112 is surrounded by an outer torch tube 120 (preferably quartz) through which coolant or plasma gas 124 is injected. The inner torch tube 112 and the outer torch tube 120 form an integrated unit 122 known as the demountable torch. Downstream of the torch injector 100 is an interaction region 128 through which the aerosol to be studied passes, in which the interaction region 128 is surrounded by RF coils 132. Alternatively, the interaction region 128 may comprise a flame or a plasma that is not inductively coupled, e.g. a microwave induced plasma. The inner torch tube 112 and the outer torch tube 120 are located within a torch box 136. A connector 104 leading to the spray chamber interfaces with a demountable torch interface 140 as shown in FIG. 2A. The optimum RF power and (Ar) injector gas flow rate for this nebulization system were 1.2 kW and 0.9 L/min, respectively.

Figure 2B:
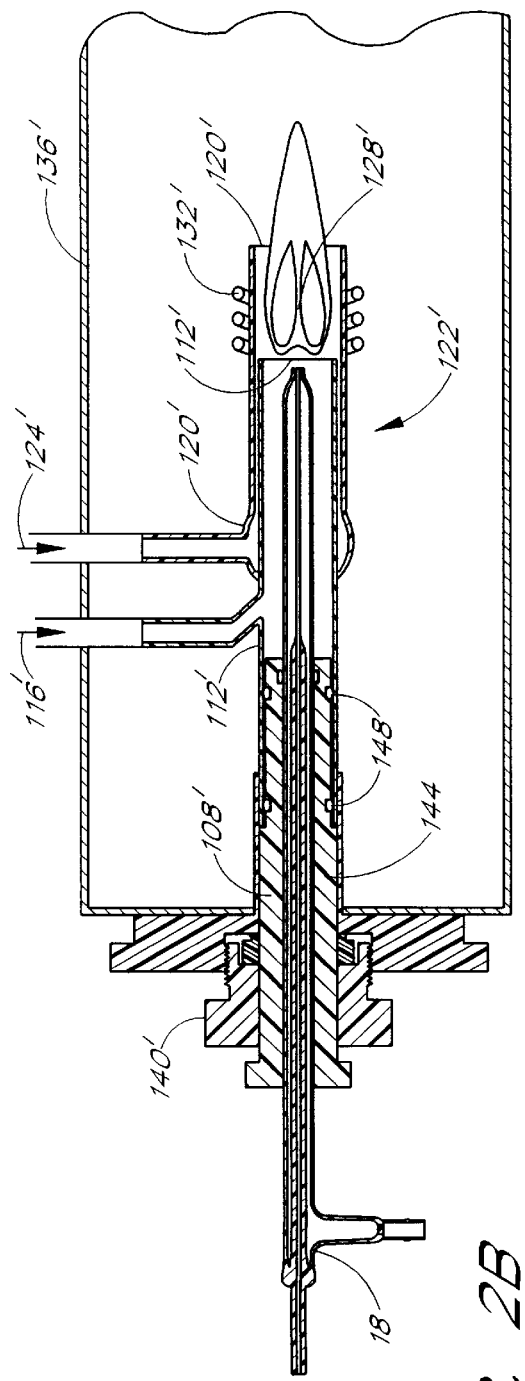
Figure 2C:
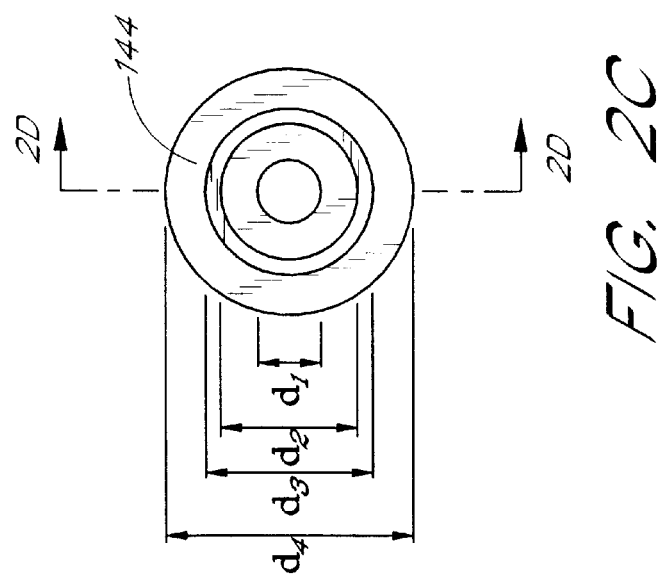
Figure 2D:
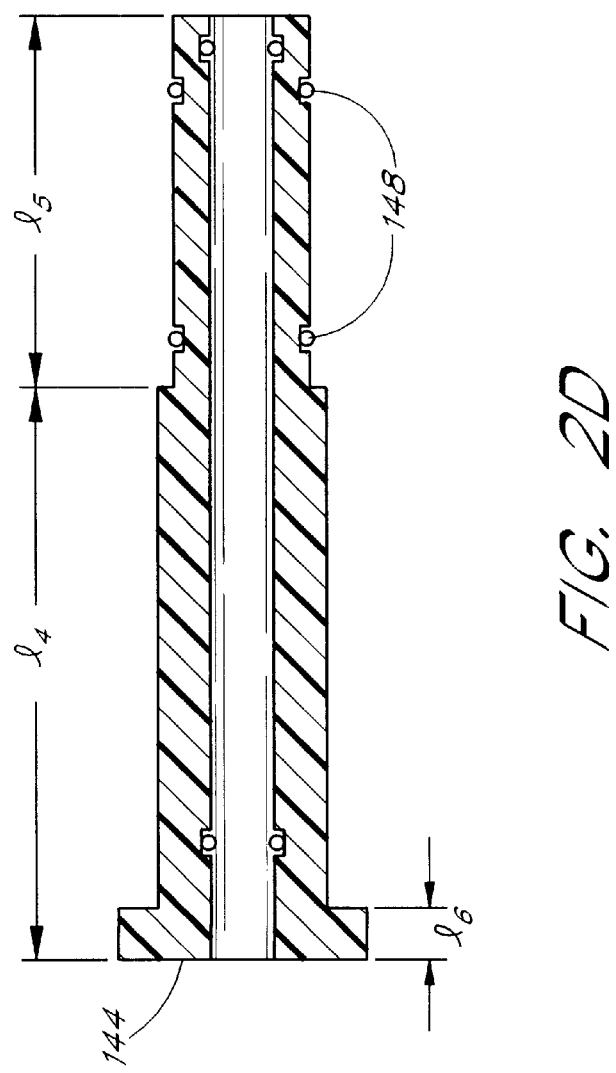

The setup used to study the DIHEN 18 is shown in FIG. 2B and is substantially analogous to the setup shown in FIG. 2A used with the cross flow pneumatic nebulizer. In particular, a demountable torch adapter 108', a demountable torch 122' (including an inner torch tube 112' and an outer torch tube 120'), an interaction region 128', RF coils 132', a torch box 136', and a demountable torch interface 140' function substantially like their unprimed counterparts. In addition, an acetal homopolymer adapter 144 (Delrin®, E.I. DuPont, Wilmington, Del., USA, see FIGS. 2C and 2D) accommodates the DIHEN 18 within the demountable torch 122' and the torch interface 140'. Preferred dimensions of the adapter 144 are 6 mm ($d_1$), 13 mm ($d_2$), 16 mm ($d_3$), 24 mm ($d_4$), 55 mm ($l_4$), 36 mm ($l_5$), and 5 mm ($l_6$). The DIHEN 18 is inserted into the adapter 144 and positioned 2 mm away from (i.e. upstream of) the end of the inner torch tube 112'. The distance between the nozzle 52 and the terminus of the outer torch tube 120' is 26 mm. Two O-rings 148 center the DIHEN 18 within the demountable torch 122'. The sample 44 to be studied (generally a liquid) passes out of the sample output port 46, whereupon it interacts with (is nebulized by) the injector gas 29 to form an aerosol which flows into the interaction region 128'. The rate at which liquid passes through the sample output port 46 is preferably in the range of 0.5–1000 microliters/min, but may also be in the ranges of 0.5–500 or 0.5–100 microliters/min. As discussed below, the operating conditions for the DIHEN system of FIG. 2B differed substantially from the setup of FIG. 2A, which is used for the conventional nebulizer-spray chamber system.

Phase-Doppler Particle Analyzer (PDPA) for Aerosol Diagnostics. For aerosol diagnostic studies, a 2D PDPA (Aerometrics Inc., Sunny Vale, Calif., USA) was used, which is not shown in the figures. The PDPA included a 300-mW argon ion laser (Model 5500A-00, Ion Laser Technologies, Salt Lake City, Utah, USA), a fiber PDA detector unit (Model RSA1000-P, Aerometrics Inc.) incorporating three PMTs, and a velocity extension unit (Model RSA1000-L, Aerometrics Inc.) having one PMT. The PMTs were operated at 500 V. The receiver (Model RCV2208, Aerometrics Inc.) was held at a forward scattering angle of 300 with respect to the transmitter (Model XMT204-2.1, Aerometrics Inc.) by placing both the receiver and transmitter on separate 15° inclined platforms. This allowed orienting the DIHEN 18 horizontally as it is used in ICPMS. The system software (Dataview 0.99g), installed on a 120-MHz PC (Model P5-120, Gateway 2000, North Sioux City, S.Dak., USA), allowed simultaneous measurements of droplet size and velocity on a spatially-resolved basis. The PDPA was calibrated at each experimental condition with a zero-phase simulated signal from a 40 MHz diode laser to compensate for phase-shifting inherent in the processing electronics and differing transit times in the dynode chains of the PMTs. The system was used with a 2× beam expander (Model XPDO404-1, Aerometrics Inc.) to measure droplet sizes in the range of 0.5 to 85 µm and droplet velocities in the range of −73 to 73 m/s. The size dynamic range of the system is 50:1. Because no droplets with diameters above 25 µm were observed, a sub-range of 0.5 to 25 µm was chosen for these studies.

The droplets produced by the DIHEN 18 were probed 15 mm from the nozzle 52 along the centerline of the aerosol. This probing spot is located in the load coil 132' region, 11 mm upstream of the end of the demountable torch 122'. To prevent the scattering of laser radiation from the quartz demountable torch 122', the aerosol was examined in the absence of the demountable torch. Droplet velocities were measured both axially (along the centerline of the aerosol) and radially (perpendicular to the centerline of the aerosol). For each experimental condition, approximately 10,000 droplets were sampled to determine the droplet size and velocity distributions. The Sauter mean diameter, defined as the volume to surface area ratio ($D_{3,2}$), was used to express droplet size distribution. Values of $D_{3,2}$ and mean velocities represent an average of 5 measurements. The precision of $D_{3,2}$ values ranged from 1.7 to 4.1 %RSD, and the precision of mean velocities ranged from 0.8 to 4.0%RSD. The DIHEN 18 described herein can, depending upon operating conditions, produce an aerosol consisting substantially of droplets having a Sauter mean diameter of less than about 15 or even 10 microns.

Microscale Flow Injection-ICPMS. For µFI-DIHEN-ICPMS experiments, a computer actuated 6-way flow injection valve 200 (FIG. 9) was used with a 20 µL sample loop 204. Sample 44 was loaded into the sample loop 204 with a peristaltic pump 208 and delivered to the DIHEN 18 with a pump 212 (specifically, a 4 channel peristaltic pump for solution flow rates of 85 µL/min via, and a syringe pump for flow rates between 5 and 42 µL/min, as discussed above). The injector gas flow rate was 0.25 L/min. The injection valve 200 was controlled by a valve control module 216, and one of the ports of the injection valve 200 was directed to a waste container 220.

The dead volume from the injection valve 200 to the nozzle 52 of the DIHEN 18 was reduced to <8.5 µL by inserting a 260 mm length of 0.008" i.d.×0.016" o.d. PTFE tubing, which is not shown in the figures, directly into the back of the DIHEN capillary tube 24 to the point where the capillary tapers. The dead volume can be reduced to less than 2 µL in a similar fashion using narrower bore PTFE tubing. To connect this microbore tubing to the injection valve 200, a 0.020" i.d.×¹⁄₁₆" o.d. FEP tubing sleeve (Upchurch Scientific, Oak Harbor, Wash., USA), which is not shown in the figures, was placed over PTFE tubing. The ICPMS data acquisition parameters for the µFI-mode are listed in Table 1. The µFI-ICPMS system was optimized daily through operating the system in a continuous flow mode. Peak heights and areas were determined by exporting data files as signal response versus time in ASCII format. The data were then analyzed using a commercial statistics package (Microcal Origin 3.73, Microcal Software, Inc., Northampton, Mass., USA).

Reagents. For analytical figures of merit, a 10 ng/mL-17 multi-element solution was prepared by diluting 1000-µL/mL stock solutions with a 2% solution of high-purity nitric acid (Fisher Scientific, Pittsburgh, Pa., USA) in 18-MΩ-cm distilled deionized water (DDW). For the µFI measurements, a 10 ng/mL solution of Cr, V, and Co was prepared from 1000-µL/mL stock solutions in 2% $HNO_3$ as described above. For the aerosol diagnostic studies, only DDW was used.

Figure 3A:
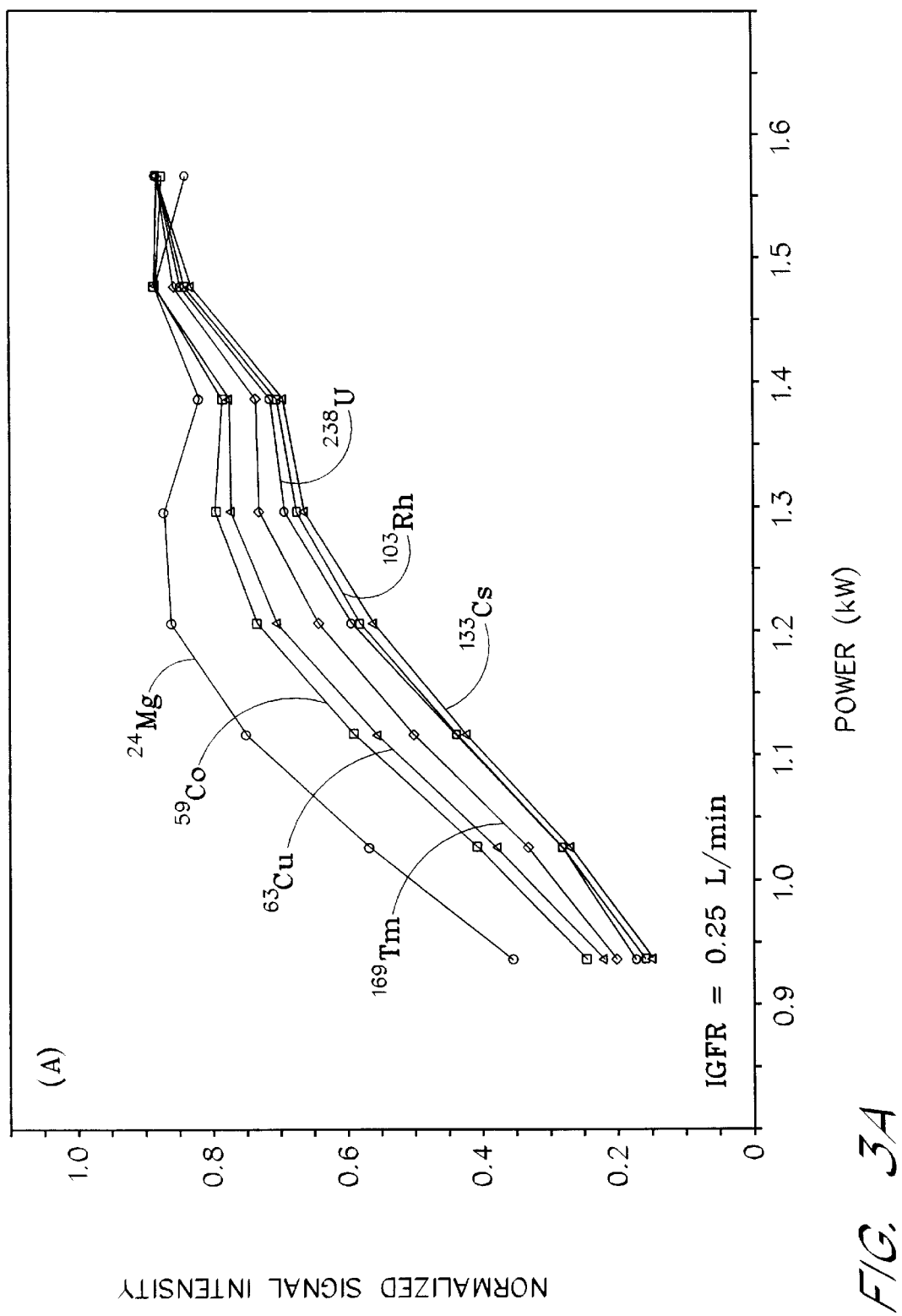
Figure 3B:
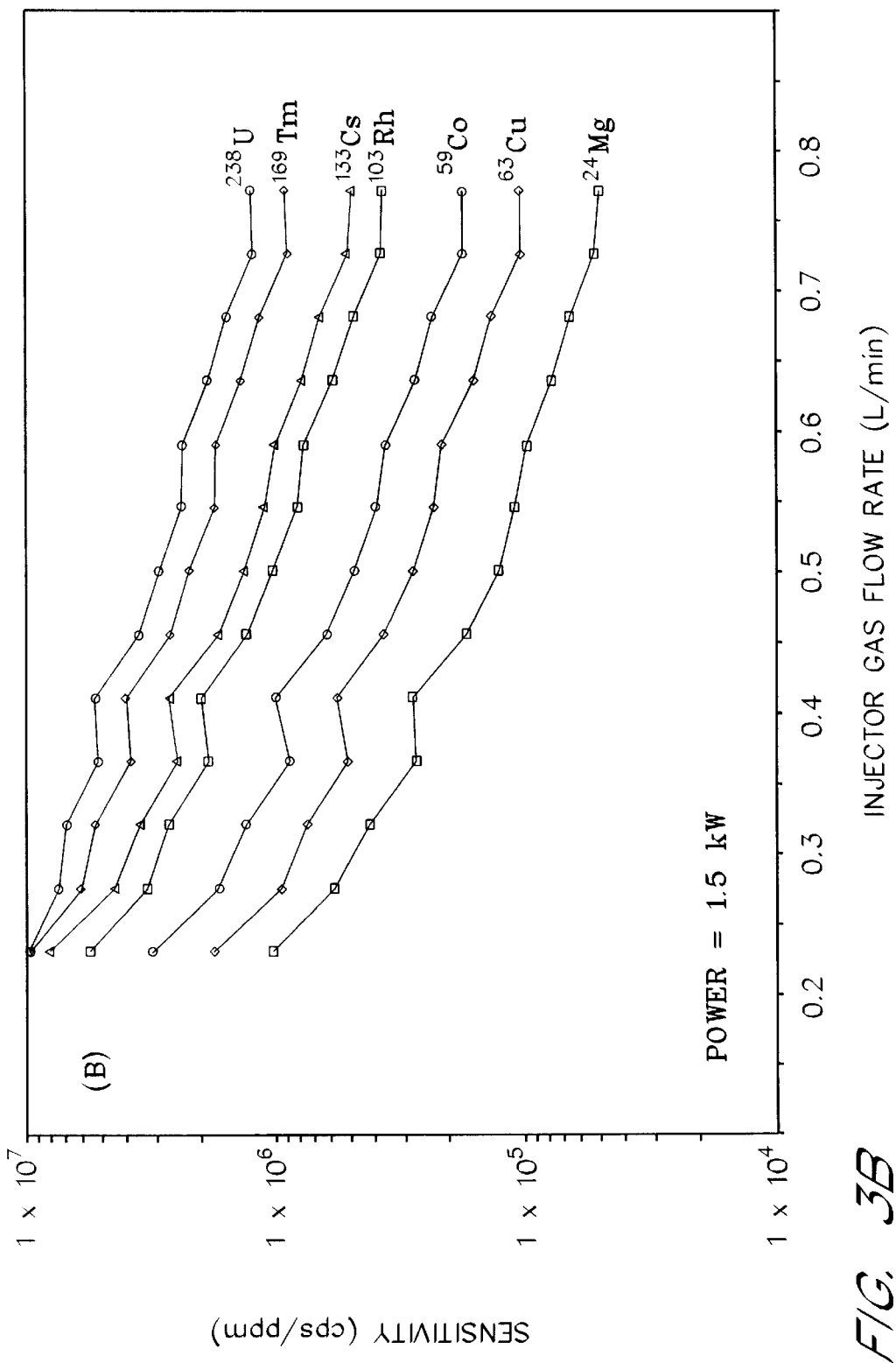

Optimization of ICPMS Experimental Parameters. Plots of normalized signal intensity as a function of RF power are shown in FIG. 3A for seven elements across the mass range. For these measurements, the solution uptake rate and the injector gas flow rate were 11 µL/min and 0.25 L/min, respectively. In all cases, maximum signal intensities were achieved at 1.5–1.6 kW for the DIHEN 18, and thus an RF power of 1.5 kW was selected for analytical measurements. Maximum sensitivity across the entire mass range was found at very low injector gas flow rates (FIG. 3B). At injector gas flow rates less than 0.2 L/min, the plasma became unstable and began to flicker. An injector gas flow rate of 0.25 L/min was chosen for the remaining studies. As discussed above, in contrast to the DIN, the DIHEN 18 requires no auxiliary nebulizer gas to confine the aerosol to the axial channel of the plasma. Visual observation of the well-known yttrium "bullet" revealed that the aerosol was well confined to the axial channel.

Detection Limits and Sensitivities. The detection limit is defined as the concentration giving a signal equivalent to 3 times the noise. Noise was calculated from the standard deviation of 11 replicate measurements of the background intensity using a 1-s integration time per replicate. The background intensity was measured at the same m/z used to generate the specific calibration curve.

The detection limits and sensitivities measured with the DIHEN 18 are given in Table 2 for 17 elements across the mass range. Table 2 also contains results obtained with the conventional setup of FIG. 2A, without aerosol desolvation at both 1000 and 85 µL/min solution uptake rates. For comparison, detection limits reported for Ar ICPMS with the conventional HEN (see S- H. Nam et al., J. Anal. At. Spectr., vol. 9, pp. 1357–1362, 1994) without aerosol desolvation, also are listed in column 3 of Table 2.

Two major observations can be made from the data under columns 4 to 9 in Table 2. First, detection limits with the DIHEN 18 (85 µL/min) are similar to, or improved over those with the crossbow nebulizer (1 mL/min). This finding, equally applicable to sensitivity data, indicates that the DIHEN 18 is at least 10 times more efficient in aerosol production at 85 µL/min uptake rate compared to the conventional crossflow PN at 1 mL/min. Second, the detection limits obtained with the HEN and DIIIEN 18 are comparable at 85 µL/min. This indicates that the direct introduction of the aerosol into the plasma with the DIHEN 18 and the associated solvent effects apparently have no significant effect on plasma characteristics. However, this statement may not be applicable to Ar ICPMS instruments that are not equipped with an electronically balanced induction coil for diminishing interdependence of parameters and interface-related discharges. Importantly, the reduction in the sample uptake rate from 1 mL to 85 µL/min did not compromise the relative detection limits of the DIHEN 18; rather, a 12-fold improvement in the absolute detection limits were generally realized compared to the results obtained with the conventional crossflow PN. Previous studies have also shown similar improvements in the absolute detection limits obtained with the DIN.

For comparison purposes, the crossflow PN also was operated at 85 µL/min, with the results shown in Table 2, columns 6 and 9. When the crossflow PN was operated at reduced solution uptake rate, detection limits and sensitivities were impaired by factors of 4–36 and 4–7, respectively, in comparison with conventional operation at 1 mL/min. A direct comparison of both nebulizers at a solution uptake rate of 85 µL/min shows the DIHEN 18 offers detection limits which are 3–100 times superior and sensitivities which are 3–27 times superior to the crossflow PN. This finding affirms the benefits of devices specifically designed for operation at reduced solution uptake rate.

Figure 4:
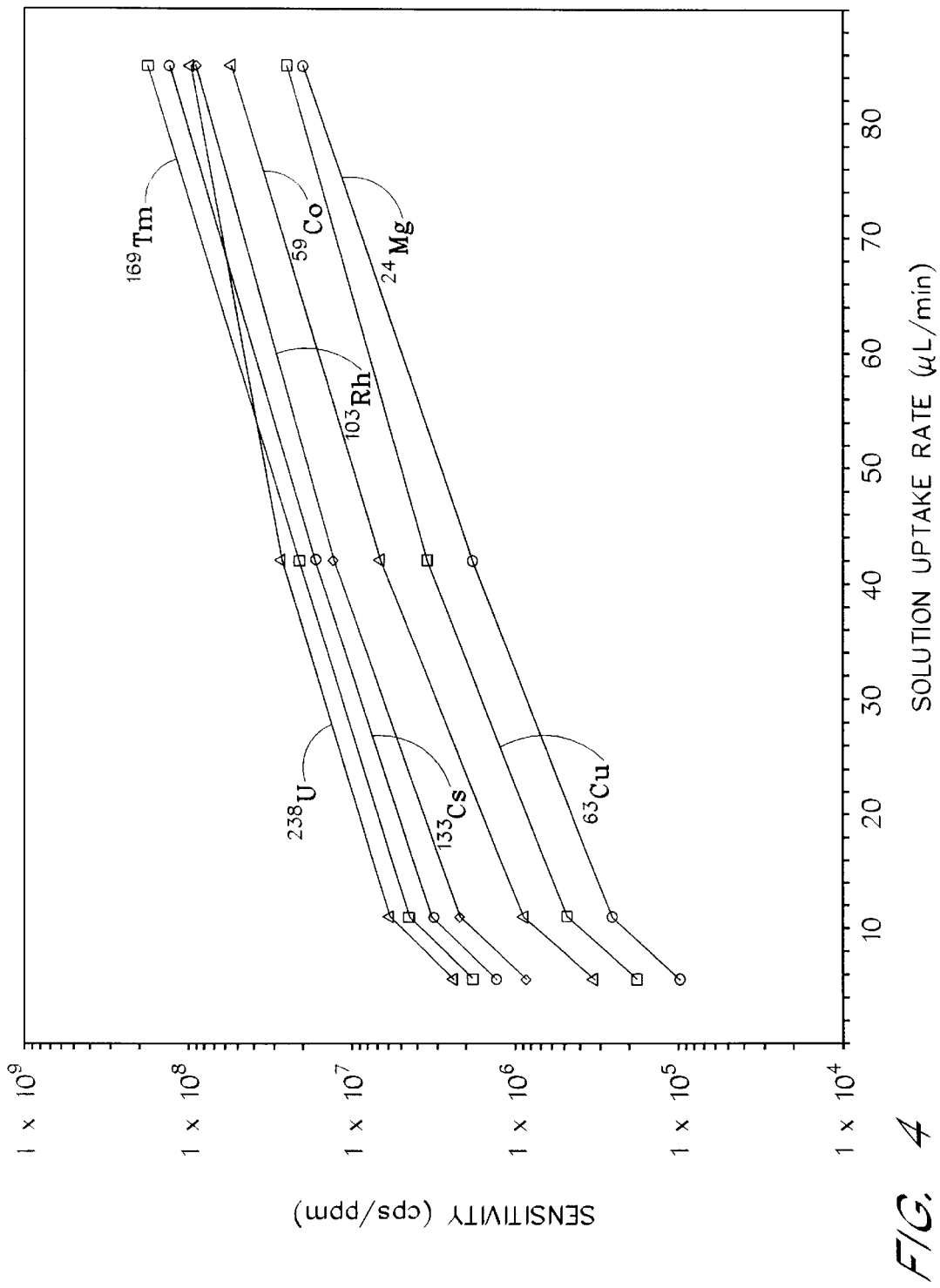

The effects of solution uptake rate on detection limits and sensitivities obtained with the DIHEN 18 are shown in Table 3 and FIG. 4, respectively. These results were obtained at operating conditions optimized for nebulization at 85 μL/min. The solution uptake rate has a significant effect on the detection limits and sensitivity at uptake rates less than 85 μL/min. Generally, the detection limits and sensitivities were degraded by a factors of 10–750 and 20–270, respectively, as the solution uptake rate was reduced from 85 to 5.6 μL/min. Presumably, these results should be improved by optimizing the conditions at reduced uptake rates. For the conventional HEN used with the Scott-type spray chamber, no significant effect on the detection limits was noted, except for an uptake rate less than 30 μL/min (see S- H. Nam et al, J. Anal. At. Spectr., vol. 9, pp. 1357–1362, 1994). Note that the capillary i.d, the capillary wall thickness, and the annulus area for the HEN were slightly smaller than those for the DIHEN 18. Thus, one should expect reduced gas-liquid interaction for the DIHEN 18 at low uptake rates as compared to the HEN, which is exacerbated by operating the DIHEN at a lower injector gas 29 flow (0.25 L/min) than the HEN (1 L/min).

As discussed above, both the DIN and the DIHEN 18 inject 100% of the sample 44 into the plasma. However, the detection limits obtained in this work with the DIHEN 18 are nearly 2 times lower than results reported for the DIN (see Y. Liu, V. Lopez-Avila, J. J. Zhu, and D. R. Wiederin, "Capillary Electrophoresis Coupled On-Line with Inductively Coupled Plasma Mass Spectrometry for Elemental Speciation," Analytical Chemistry, vol. 67, pp. 2020–2025, 1995). While this difference may be partly attributed to the disparities in experimental arrangements, one should not neglect the better quality of the aerosol produced by the DIHEN 18, as discussed below.

Precision. Typical data for precision arc presented in Table 2, columns 10–12 for the DIHEN 18 and the crossflow PN for 17 elements. For precision, the percent relative standard deviation (%RSD) was calculated for 11 replicate trials over a period of 7 minutes. The measured precision for the DIHEN 18 ranged from 0.4 to 1.4 %RSD for the 17 elements tested, but was typically between 0.6 and 0.8%RSD. Generally, the precision obtained with the DIHEN 18 was better than that obtained with the crossflow nebulizer operated at 1 mL/min (0.7 to 1.7%RSD). Precision obtained with the crossflow nebulizer obtained at reduced flow (85 μL/min) ranged from 0.9 to 8.6%RSD.

With conventional sample introduction systems such as the crossflow nebulizer, signal imprecision is attributed to several factors such as turbulence effects in the spray chamber, pressure pulses from the spray chamber waste container (not shown in the figures) and the solution pumping system, fluctuations in the local velocity of the droplets or their diameter, and instabilities of the plasma itself. For example, Houk and coworkers (see D. R. Wiederin, F. G. Smith, and R. S. Houk, "Direct Injection Nebulization for Inductively Coupled Plasma Mass Spectrometry," Anal. Chem., vol. 63, pp. 219–225, 1991), found that precision obtained with the DIN was degraded by a factor of four when the DIN was operated with a spray chamber. Similarly, by eliminating the spray chamber, several of these noise sources are eliminated when the DIHEN 18 is used. Considering that the data disclosed herein were obtained in the peak hopping mode using only one point per peak, even better precision may be realized by averaging results over three points/mass peak.

Oxide and Doubly Charged Species. For conventional nebulizers, both the oxide and the doubly charged ratios are strong functions of the injector gas flow rate, and can be reduced by lowering the injector gas flow, using mixed-gas plasmas, or aerosol desolvation. For example, using an USN, an oxide ratio of 50.4% and 0.84% for Ce at an injector gas flow rate of 1 and 0.8 L/min, respectively, has been reported (see T. W. Avery, C. Chakrabarty, and J. J. Thompson, "Characterization and Optimization of a Direct Injection Nebulizer for Introduction of Organic Solvents and Volatile Analyte Species into an Inductively Coupled Plasma," Applied Spectroscopy, vol. 44, pp. 1690–1698, 1990.) Because 100% of the sample is sprayed directly into the plasma with the DIHEN 18 or the DIN, one should expect a greater level of polyatomic ions compared to conventional nebulization using a cooled spray chamber or desolvation device. The increase in polyatomic ion levels with the DIN and DIHEN 18 is attributed to an increased solvent load and the introduction of the primary rather than tertiary aerosol into the plasma.

Figure 5A:
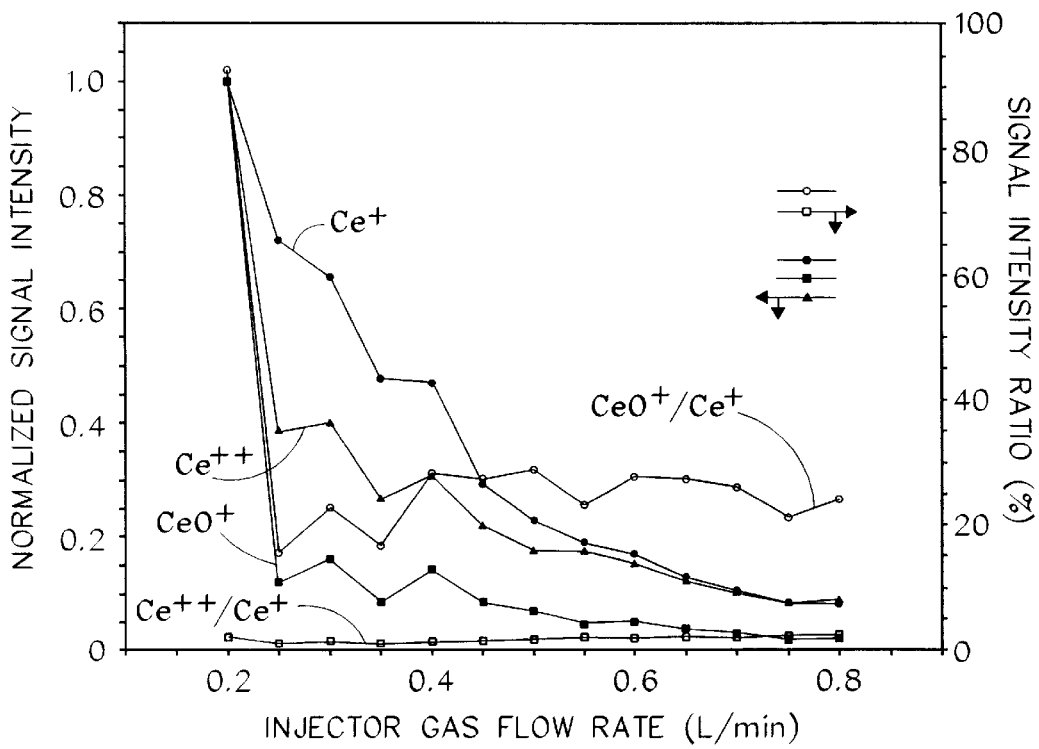
Figure 5B:
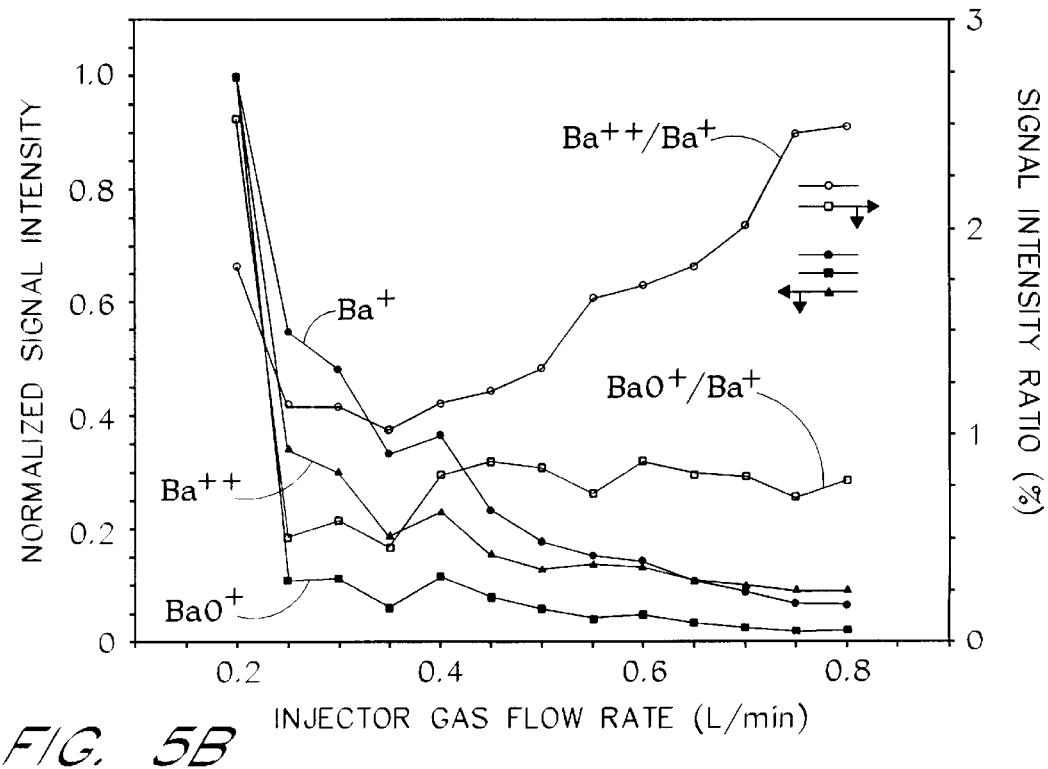

The data in FIGS. 5A and B show normalized intensities of metal ions ($M^+$) and ratios of the oxides and doubly charged ions to singly charged ions ($MO^+/M^+$ and $M^{++}/M^+$) for the DIHEN 18 as a function of the flow rate of injector gas 29 at an uptake rate of 11 μL/min. The elements Ba and Ce were selected for this experiment because they are easily ionized in the Ar ICP, and their oxide ions represent nearly two extreme cases in terms of bond strength, with Ce forming one of the strongest oxides (bond energy for $CeO^+$ is 8.8 eV). Both the $MO^+/M^+$ and $M^{++}/M^+$ are at a minimum for an injector gas 29 flow of 0.35 L/min. At higher injector gas 29 flow rates, the $M^{++}/M^+$ were enhanced, but the $MO^+/M^+$ levels remained relatively constant above 0.4 l min$^{-1}$. Below 0.25 L/min, the $MO^+/M^+$ and $M^{++}/M^+$ rose significantly. Presumably, the injector gas 29 flow rate was insufficient to transfer the analyte ions into the sampling cone of the ICPMS instrument.

As discussed above, maximum sensitivities and optimal detection limits were obtained at an injector gas flow of 0.25 L/min. Thus, it is important to examine the relative magnitude of oxides and doubly charged species under this condition. Values of $MO^+/M^+$ and $M^{++}/M^+$ are shown in Table 4 for four solution uptake rates (5.6, 11, 42, and 85 μL/min). Note that oxide levels decreased from 1.1% to 0.55% for Ba, and from 48 to 16% for Ce as the solution uptake rate was reduced from 85 to 5.6 μL/min. For comparison, the oxide ratios obtained with the DIN under optimal sensitivity conditions (120 μL/min) were in the range of 50 to 100% for refractory metal oxides such as La and U. However, Houk and coworkers (see D. R. Wiederin, F. G. Smith, and R. S. Houk, "Direct Injection Nebulization for Inductively Coupled Plasma Mass Spectrometry," Anal. Chem., vol. 63, pp. 219–225, 1991) found that they could reduce these oxide levels to 6.6 and 7.2%, for $LaO^+/La^+$ and $UO^+/U^+$, respectively, through changing the sampling depth to 26 mm. Similar results are obtained for the DIHEN 18 when the sampling depth is increased to 21 mm where $CeO^+/Ce^+$ was reduced to 8%.

Droplet Sizes and Velocities with the DIHEN 18. The extent of desolvation, vaporization, excitation, and ionization processes in the Ar ICP is highly dependent on the size and velocity of the droplets presented to the plasma. The ideal aerosol for ICP spectrometries consists of monodisperse droplets that travel with the same velocity. Any deviations from the cited criteria contribute to inefficient utilization of the sample, reduced sensitivity, increased interferences, and imprecision. Changes in the solution uptake rate and the injector gas flow may shift the droplet size-velocity distribution and compromise analytical performance indices.

In FIG. 3B, the effect of injector gas 29 flow rate on sensitivity was presented for the DIHEN 18. The correlation between sensitivity and the aerosol characteristics is now considered. Representative droplet-size distributions and droplet-velocity distributions are shown in FIGS. 6A–D, 7A–D, and 8A–D, at injector gas flow 29 rates ranging from 0.2 to 1.0 L/min. Both axial and radial velocities are depicted in FIGS. 8A–D. A number of interesting observations are to be made. First, the $D_{3,2}$ value was reduced as the injector gas 29 was increased, but the droplet mean velocities, both the axial and radial components, were increased at higher injector gas flow. Second, at low gas flow rates, the droplet-size distribution, normalized as count percent, was multimodal, but the distribution became nearly lognormal at higher gas flow. For an injector gas 29 flow rate of 0.2 L/min, peaks appeared at approximately 2, 4, 7, 10, and 13 μm, exhibiting a behavior similar to the OCN. Microscopic inspection of the capillary tube 24 indeed revealed DIHEN capillary oscillation at low injector 29 gas flow rates. As the injector gas 29 flow rate was increased, the peaks became less defined, and the multimodal distribution shifted gradually to a unimodal distribution. As the result of this shift, the $D_{3,2}$ values were reduced from 10.1 to 7.6 μm while the droplet axial mean velocity was increased from 13 to 37 m/s.

The third observation is concerned with the distribution of axial and radial velocities. These distributions (FIGS. 8A–D) may reveal why sensitivity was sharply reduced at increased injector gas flow although generally smaller droplets were introduced into the plasma with the DIHEN 18. Evidently, sensitivity should be reduced as the sample-plasma interaction time is diminished at higher droplet velocities. Note, however, both the axial and radial velocity distributions became wider at higher injector gas 29 flow. In other words, the aerosol trajectory is confined to the axial channel at low injector gas 29 flow rates, but it is broadened significantly as the injector gas flow rate is increased. In short, the narrower axial and radial velocity distributions at low injector gas 29 flow result in enhanced desolvation-vaporization-excitation-ionization of the sample droplets in the plasma, and consequently improved sensitivity. However, this statement must be treated with caution. With the ICP on, the inward radial gas flow in the center of the ICP affects aerosol distribution in the plasma.

Figure 9:
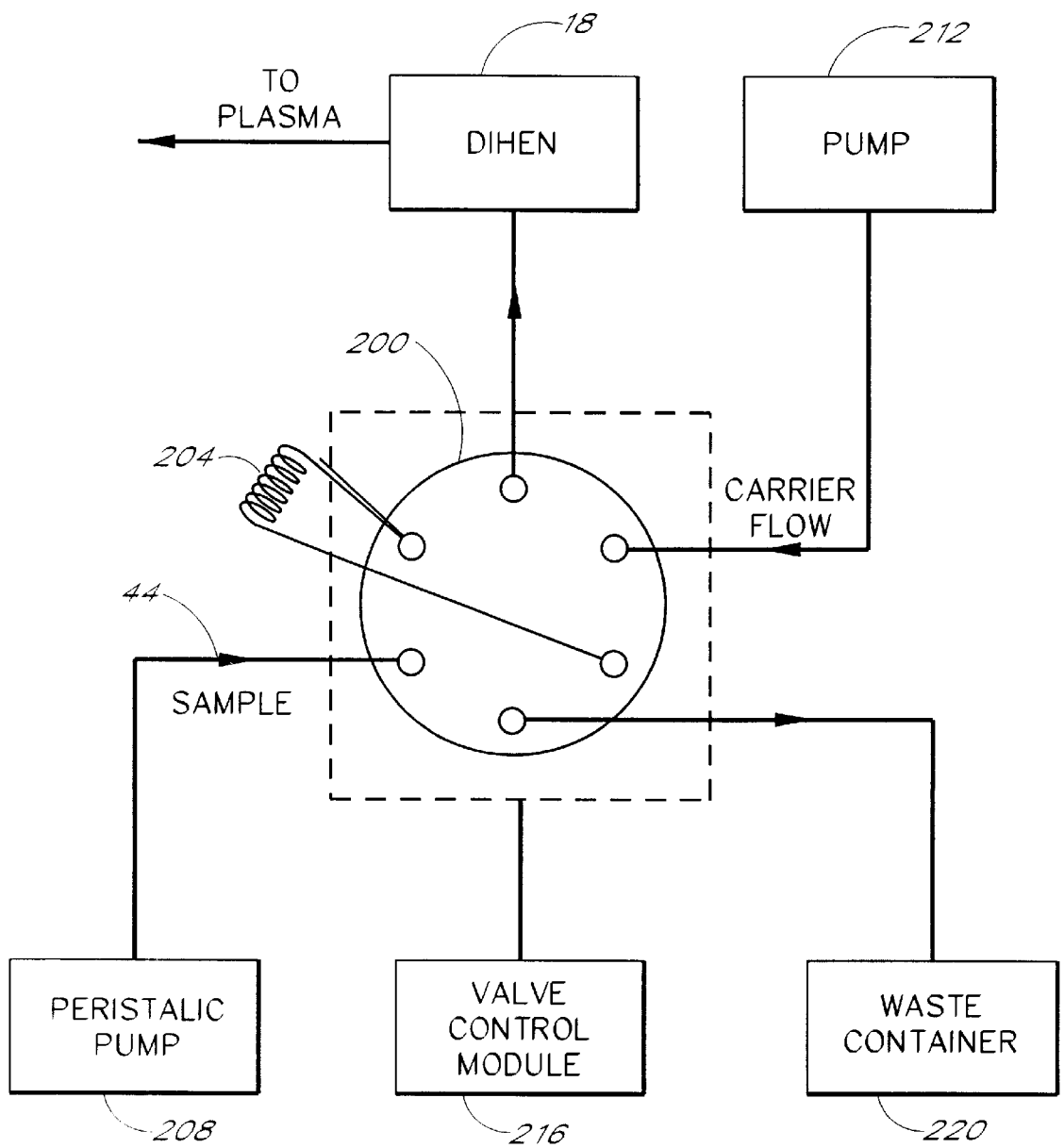
Figure 10:
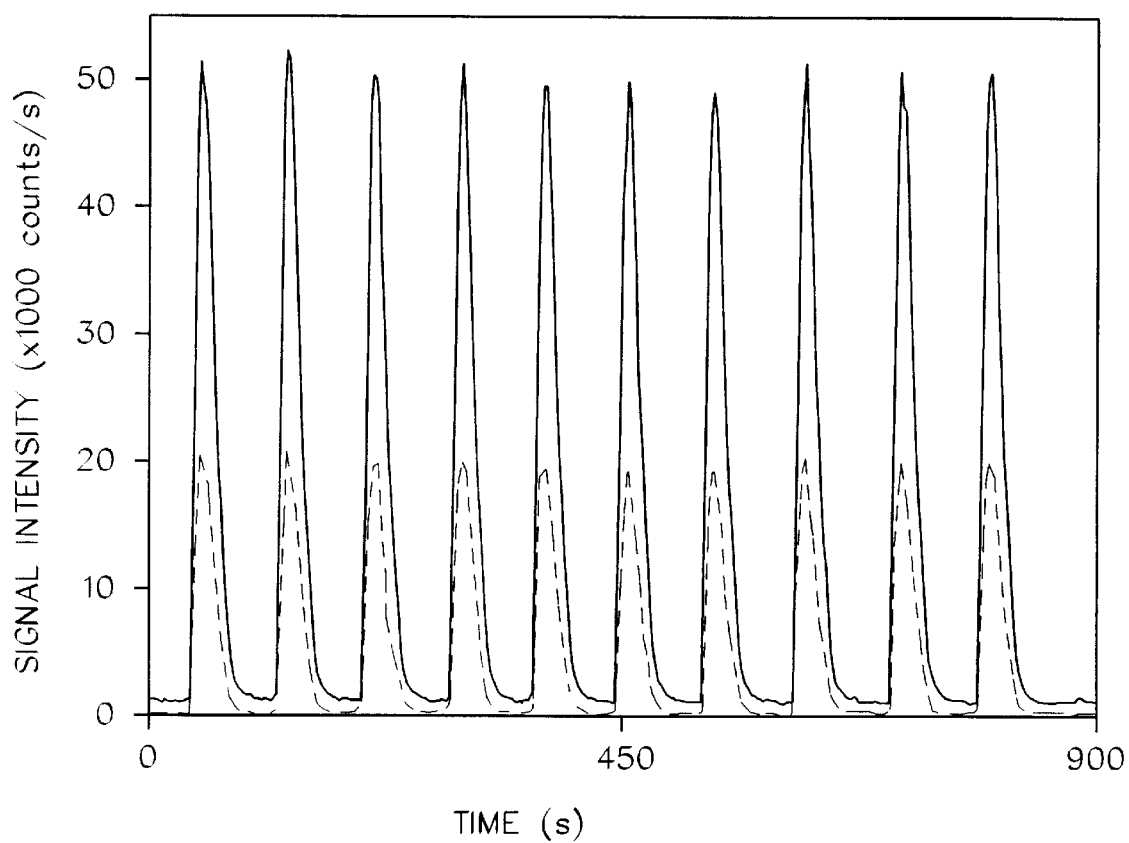

Microscale Flow Injection-ICPMS. A schematic flow diagram for the μFI-ICPMS system is shown in FIG. 9. The response of the system was first evaluated using a 10 ppb solution of Cr in 2% $HNO_3$ which was monitored at m/z 50 and 53, due to substantial interference from $^{40}Ar^{12}C$ which inhibits monitoring the major isotope of Cr at m/z 52. Typical peak profiles are presented in FIG. 10 for the transient signals obtained for 10 repeat injections (200 pg Cr/injection). The peak-to-peak precisions (N=10) for peak areas are 2.8 and 2.5%RSD, respectively for $^{53}Cr$ and $^{50}Cr$. The peak-to-peak precisions (N=10) for peak heights are 1.9 and 2.3 %RSD, respectively for $^{53}Cr$ and $^{50}Cr$. Precision for the isotopic ratio $^{50}Cr/^{53}Cr$ was 1.3% and 0.9%RSD, based on area and height measurements, respectively. The precision for isotope ratios measured previously with a HEN operated in the μFI mode are slightly better than those discussed herein (S. A. Pergantis, E. M. Heithmar, and T. A. Hinners, "Microscale Flow Injection and Microbore High-Performance Liquid Chromatography Coupled with Inductively Coupled Plasma Mass Spectrometry via a High-Efficiency Nebulizer," Analytical Chemistry, vol. 67, pp. 4530–4535, 1995). However, the previous results of Pergantis et al. were obtained for major lead isotope ratios ($^{207}Pb/^{208}Pb$ and $^{206}Pb/^{208}Pb$) at higher concentrations (approx. 7.5 times).

Analysis of Cr Bound to DNA. Samples of Cr bound to DNA (Cr-DNA) were prepared by incubating primary human lung epithelial cells in the presence of 0.5 mM $Na_2CrO_4$ for 2 hours. Sodium dodecasulfate (SDS) was then added to lyse the cells and to solubolize and remove the proteins. RNase was added to digest the RNA and the remaining Cr-DNA was extracted with chloroform/phenol (1:1 v/v). After precipitation with 95% ethanol (0° C.), the Cr-DNA was reconstituted in Tris EDTA buffer (10 mM Tris, 1 mM EDTA, pH8). The purity and quantity of DNA was determined by optical density measurements at 260 and 280 nm. For these preliminary studies, the Cr-DNA sample was then digested by the restriction enzyme ECOR1 and then diluted to a final volume of 2 mL with Tris EDTA buffer. The sample was analyzed as is, i.e., without further digestion by microwave or other techniques.

Figure 11:
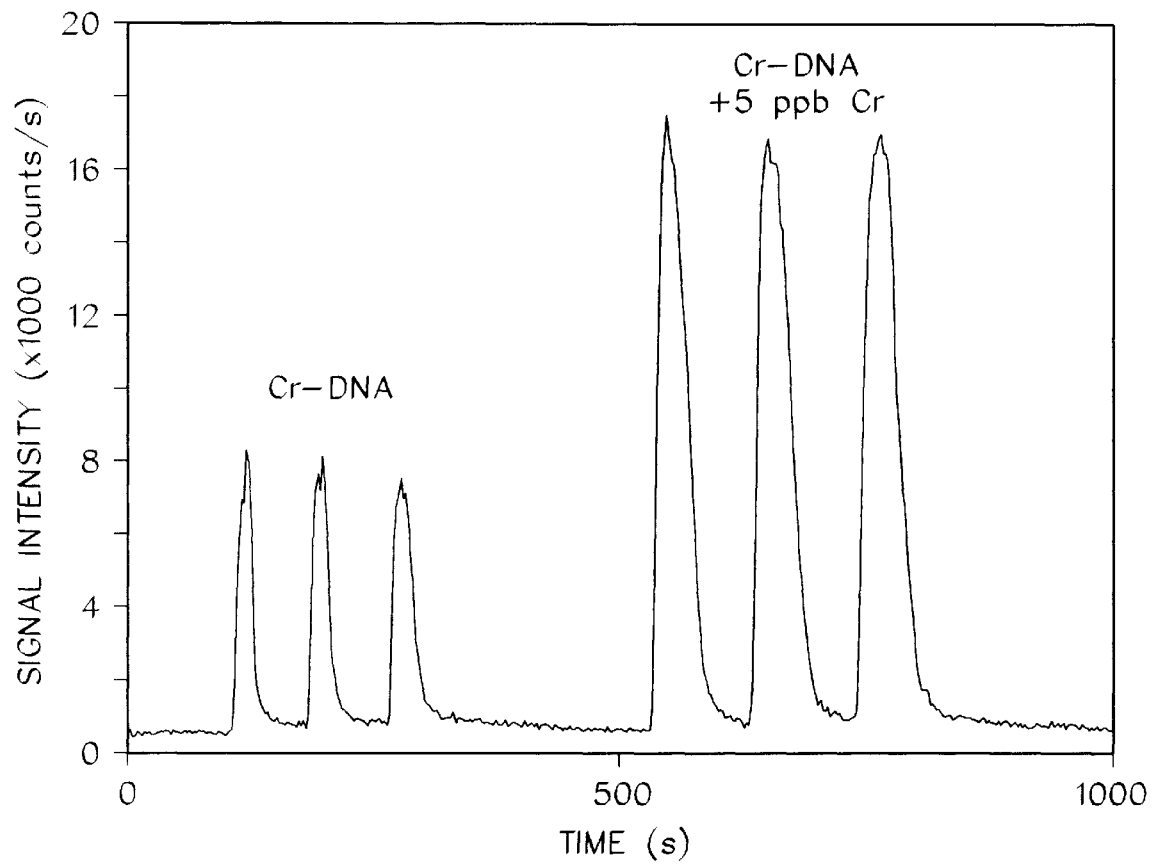

The determination of Cr with quadrupole-based ICPMS instruments is particularly difficult owing to the large number of potential isobaric interferences from molecular species. As discussed above, spectral interference from $^{40}Ar^{12}C$ and $^{40}Ar^{14}N$ precluded monitoring $^{52}Cr$ and $^{54}Cr$, respectively. Additionally, interference from $^{34}S^{16}O$, $^{32}S^{18}O$, and $^{33}S^{17}O$ species derived from protein, SDS, and enzyme contamination precluded monitoring $^{50}Cr$. Thus, $^{53}Cr$ was chosen for the determination of Cr in Cr-DNA. Peak profiles are shown in FIG. 11 for a 1:1 dilution of Cr-DNA and 2% $HNO_3$, and a 1:1 dilution of Cr-DNA and 10 ppb Cr in 2% $HNO_3$. Based on this one point standard addition, the concentration of Cr was determined to be 2.38±0.12 ppb, corresponding to 47.6±2.4 pg of Cr per injection. The limit of detection (3σ) for the technique is 980 fg per injection using a 20 μL sample loop.

A comparison of the Cr-DNA peak profiles (FIG. 11) with the standard solution peak profiles (FIG. 10) reveal three important differences. First, the Cr-DNA peak shapes are less well defined compared to those for the standard solutions. Second, the Cr-DNA response is much noisier than with the 2% $HNO_3$ solutions. Third, a suppression of the Cr response is noted. These differences likely occur because of changes in the aerosol generation efficiency with the Cr-DNA sample only diluted 1:1 with 2% $HNO_3$. These differences might be eliminated by reducing the sample size or through further sample digestion either enzymatically, or by microwave.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes which come within the meaning and range of equivalency of the claims are to be embraced within that scope.

TABLE 1

Operating Conditions for the Ar ICPMS Instrument

| | |
|---|---|
| ICPMS System | PE-Sciex Elan 6000 |
| RF power, W | 1500*, 900–1600 |
| Nominal frequency, MHz | 40 |
| RF generator type | Free-running |
| Induction coil circuitry | 3-turn coil, PLASMALOK ™ |
| Sampling depth (above load coil), mm | 11* |
| Sampler (orifice diameter, mm) | Nickel, 1.1 |
| Skimmer (orifice diameter, mm) | Nickel, 0.9 |
| Plasma gas 124 flow rate, L/min | 15 |
| Auxiliary gas 116 flow rate, L/min | 1.2 |
| Sample Introduction System | DIHEN 1 8, see Figures 1A, 1B, 1C and specification |
| Capillary tube 24 i.d., mm | 0.082 |
| Capillary tube 24 wall thickness at distal end, mm | 0.035 |
| Area of annular region 56, mm$^2$ | 0.0099 |
| Solution uptake rate, μL/min | 5.6–85 |
| Injector gas 29 flow rate, L/min | 0.25*, 0.2–0.8 |

| | Figures of Merit | Microscale Flow Injection |
|---|---|---|
| Solution flow mode | Continuous | Injection |
| Data acquisition parameters | | |
| Scan mode | Peak hopping | Peak hopping |
| Points/mass | 1 | 1 |
| Resolution, amu | 0.7 | 0.7 |
| Sweeps/Reading | 10 | 15 |
| Readings/Replicate | 5 | 1 |
| Replicates | 11 | 500 |
| Dwell time/mass, ms | 20 | 20 |
| Integration time, ms | 1000 | 300 |

*Unless otherwise indicated.

TABLE 2

Relative Detection Limits, Sensitivity, and Precision, for the DIHEN 18 and Crossflow Nebulizers Determined at different Solution Uptake Rates.

| | | Detection Limits† (ppt) | | | | Sensitivity (Mhz/ppm) | | | Precision* (% RSD) | | |
|---|---|---|---|---|---|---|---|---|---|---|---|
| | | HEN‡ | DIHEN | Crossflow | | DIHEN | Crossflow | | DIHEN | Crossflow | |
| Element | Mass | 85 μL/min | 85 μL/min | 1000 μL/min | 85 μL/min | 85 μL/min | 1000 μL/min | 85 μL/min | 85 μL/min | 1000 μL/min | 85 μL/min |
| Li | 7 | | 2 | 15 | 200 | 8.2 | 1.6 | .37 | 0.6 | 1.1 | 1.8 |
| Mg | 24 | | 7 | 24 | 150 | 20 | 6.4 | 1.5 | 0.6 | 1.1 | 1.7 |
| V | 51 | 8 | 2 | 6 | 25 | 30 | 19 | 4.0 | 0.8 | 1.4 | 1.6 |
| Mn | 55 | 4 | 2 | 5 | 170 | 65 | 32 | 7.2 | 0.7 | 1.6 | 1.6 |
| Co | 59 | 7 | 0.9 | 2 | 39 | 56 | 26 | 5.7 | 0.8 | 1.2 | 1.3 |
| Ni | 60 | 5 | 12 | 19 | 640 | 9.9 | 4.6 | 1.3 | 0.7 | 1.6 | 4.1 |
| Cu | 63 | 5 | 10 | 9 | 320 | 25 | 10 | 2.5 | 0.6 | 0.7 | 2.0 |
| As | 75 | 55 | 17 | 12 | 54 | 4.5 | 3.4 | 0.78 | 1.3 | 0.9 | 3.9 |
| Se | 82 | | 47 | 130 | 2300 | 0.6 | 0.4 | 0.06 | 1.4 | 1.7 | 8.6 |
| Sr | 88 | | 0.9 | 0.9 | 29 | 95 | 51 | 12 | 0.8 | 1.0 | 1.3 |
| Rh | 103 | | 0.6 | 0.6 | 9 | 91 | 47 | 11 | 0.9 | 1.1 | 0.9 |
| In | 115 | 6 | 0.6 | 0.6 | 6 | 113 | 60 | 14 | 0.6 | 1.1 | 1.0 |
| Cs | 133 | 6 | 0.6 | 0.6 | 5 | 130 | 80 | 18 | 0.9 | 1.1 | 1.0 |
| Tm | 169 | | 0.3 | 0.3 | 4 | 178 | 106 | 23 | 0.4 | 0.9 | 1.3 |
| Pb | 208 | 7 | 5 | 2 | 20 | 76 | 40 | 8.6 | 0.5 | 1.0 | 1.2 |
| Th | 232 | 8 | 2 | 0.6 | 5 | 66 | 94 | 22 | 1.2 | 0.8 | 1.0 |
| U | 238 | 5 | 0.3 | 0.3 | 5 | 99 | 98 | 23 | 0.8 | 0.8 | 0.9 |

*Over 7 minutes, N = 11.
†Based on 3 σ of the blank solution measured at the mass of the analyte.
‡Obtained on an Elan 5000 without desolvation (S-H. Nam et al, J. Anal. At. Spectr., vol. 9, pp. 1357–1362, 1994).

TABLE 3

Relative Detection Limits (ng/L) Determined at Low Solution Uptake Rates with the DIHEN 18.

| | | Solution uptake rate, μL/min | | | |
|---|---|---|---|---|---|
| Element | Mass | 5.6 | 11 | 42 | 85 |
| Li | 7 | 1500 | 380 | 62 | 2 |
| Mg | 24 | 430 | 160 | 17 | 7 |
| V | 51 | 230 | 67 | 10 | 2 |
| Mn | 55 | 870 | 260 | 25 | 2 |
| Co | 59 | 340 | 78 | 11 | 0.9 |
| Ni | 60 | 750 | 320 | 35 | 12 |
| Cu | 63 | 160 | 130 | 12 | 10 |
| As | 75 | 650 | 180 | 52 | 17 |
| Se | 82 | 12000 | 4500 | 570 | 47 |
| Sr | 88 | 90 | 32 | 7 | 0.9 |
| Rh | 103 | 38 | 30 | 3 | 0.6 |
| In | 115 | 44 | 17 | 2 | 0.6 |
| Cs | 133 | 45 | 13 | 4 | 0.6 |
| Tm | 169 | 30 | 10 | 2 | 0.3 |
| Pb | 208 | 45 | 25 | 4 | 5 |
| Th | 232 | 26 | 5 | 2 | 2 |
| U | 238 | 20 | 7 | 2 | 0.3 |

TABLE 4

Doubly Charged and Oxide Ratios with the DIHEN 18 Measured at Different Solution Uptake Rates.

| | Solution uptake rate, μL/min | | | |
|---|---|---|---|---|
| | 5.6 | 11 | 42 | 85 |
| BaO$^+$: Ba$^+$ | 0.55% | 0.51% | 0.83% | 1.1% |
| CeO$^+$: Ce$^+$ | 16% | 16% | 26% | 48% |

TABLE 4-continued

Doubly Charged and Oxide Ratios with the
DIHEN 18 Measured at Different Solution Uptake
Rates.

Solution uptake rate, µL/min

|  | 5.6 | 11 | 42 | 85 |
|---|---|---|---|---|
| $Ba^{2+}$: $Ba^+$ | 1.4% | 1.1% | 1.5% | 1.2% |
| $Ce^{2+}$: $Ce^+$ | 1.3% | 1.2% | 1.4% | 1.5% |

Injector gas 29 flow rate = 0.25 L/min

What is claimed is:

1. A method of delivering a sample comprised of liquid for analysis by spectrometry, comprising:

providing a direct injection nebulizer that includes an elongate tubular shell having a gas input port and a gas output port, and that includes a capillary tube within the tubular shell, the capillary tube having a sample input port and a sample output port, in which the shell has a terminus at the gas output port, and the capillary tube has a terminus at the sample output port, the capillary tube terminus being substantially at or proximal to the shell terminus;

inserting the direct injection nebulizer into a torch box;

converting the liquid into an aerosol consisting substantially of droplets having a Sauter mean diameter (as determined with respect to normalized volume percent) of less than about 15 micrometers at a point along a centerline of the aerosol at a distance of 15 mm from the terminus of the shell, said converting comprising nebulizing the liquid with the gas by:

(a) outputting gas from the gas output port of the elongate tubular shell without outputting gas from an auxiliary nebulizer gas passageway; and (b) passing the liquid from the sample input port to the sample output port of the capillary tube at a flow rate substantially less than 100 µL/min by (i) drawing the liquid out of the capillary tube without a pump using the Venturi effect caused by said outputting gas from the gas output port or (ii) using a low pressure pump to supplement the Venturi effect such that pressure applied to the liquid is not substantially greater than that provided by a peristaltic pump; and directly injecting the aerosol towards an interaction region of the torch box.

2. The method of claim 1, wherein said converting comprises converting the liquid into an aerosol consisting substantially of droplets having a Sauter mean diameter (as determined with respect to normalized volume percent) of less than about 10 micrometers at a point along a centerline of the aerosol at a distance of 15 mm from the terminus of the shell, by nebulizing the liquid with the gas.

3. The method of claim 1, wherein said injecting the aerosol towards an interaction region comprises injecting the aerosol into a flame or a plasma.

4. The method of claim 1, comprising passing the liquid through the capillary tube at a flow rate between 0.5 and 100 µL/min.

5. The method of claim 1, comprising directing the aerosol towards the interaction region such that substantially all of the droplets have axial velocities less than about 80 m/s at a point along a centerline of the aerosol at a distance of 15 mm from the terminus of the shell.

6. The method of claim 1, comprising directing the aerosol towards the interaction region such that substantially all of the droplets have axial velocities on the order of 10 m/s to 40 m/s at a point along a centerline of the aerosol at a distance of 15 mm from the terminus of the shell.

7. The method of claim 1, comprising passing the liquid through the capillary tube at a flow rate between 5.6 and 85 µL/min.

8. The method of claim 1, comprising passing the liquid through the capillary tube at a flow rate between 5 and 42 µL/min.

9. The method of claim 1, wherein the direct injection nebulizer is of one-piece construction.

10. The method of claim 1, wherein the capillary tube terminates axially at the same location as the shell terminus.

11. A method of delivering a sample comprised of liquid for analysis by spectrometry, comprising:

providing a direct injection nebulizer that includes an elongate tubular shell having a gas input port and a gas output port, and that includes a capillary tube within the tubular shell, the capillary tube having a sample input port and a sample output port, in which the shell has a terminus at the gas output port, and the capillary tube has a terminus at the sample output port, the capillary tube terminus being substantially at or proximal to the shell terminus;

inserting the direct injection nebulizer into a torch box;

converting the liquid into an aerosol consisting substantially of droplets having an axial velocity less than about 80 m/s at a point along a centerline of the aerosol at a distance of 15 mm from the terminus of the shell, said converting comprising nebulizing the liquid with the gas by:

(a) outputting gas from the gas output port of the elongate tubular shell without outputting gas from an auxiliary nebulizer gas passageway; and (b) passing the liquid from the sample input port to the sample output port of the capillary tube at a flow rate substantially less than 100 µL/min by (i) drawing the liquid out of the capillary tube without a pump using the Venturi effect caused by said outputting gas from the gas output port or (ii) using a low pressure pump to supplement the Venturi effect such that pressure applied to the liquid is not substantially greater than that provided by a peristaltic pump; and directly injecting the aerosol towards an interaction region of the torch box.

12. The method of claim 11, wherein said converting comprises converting the liquid into an aerosol consisting substantially of droplets having a Sauter mean diameter (as determined with respect to normalized volume percent) of less than 15 micrometers at a point along a centerline of the aerosol at a distance of 15 mm from the terminus of the shell.

13. The method of claim 11, wherein said converting comprises converting the liquid into an aerosol consisting substantially of droplets having a Sauter mean diameter (as determined with respect to normalized volume percent) of less than 10 micrometers at a point along a centerline of the aerosol at a distance of 15 mm from the terminus of the shell.

14. The method of claim 11, comprising passing the liquid through the capillary tube at a flow rate between 0.5 and 100 µL/min.

15. The method of claim 11, wherein said injecting the aerosol towards an interaction region comprises injecting the aerosol into a flame or a plasma.

16. The method of claim 11, comprising directing the aerosol towards the interaction region such that substantially all of the droplets have axial velocities on the order of 10 m/s to 40 m/s at a point along a centerline of the aerosol at a distance of 15 mm from the terminus of the shell.

17. The method of claim 11, comprising passing the liquid through the capillary tube at a flow rate between 5.6 and 85 µL/min.

18. The method of claim 11, comprising passing the liquid through the capillary tube at a flow rate between 5 and 42 µL/min.

19. The method of claim 11, wherein the direct injection nebulizer is of one-piece construction.

20. The method of claim 11, wherein the capillary tube terminates axially at the same location as the shell terminus.

21. A method of delivering a sample comprised of liquid for analysis by spectrometry, comprising:

provideing a direct injection nebulizer of one-piece construction that includes an elongate tubular shell having a gas input port and a gas output port, and that includes a capillary tube within the tubular shell, the capillary tube having a sample input port and a sample output port, in which the shell has a terminus at the gas output port, and the capillary tube has a terminus at the sample output port, the capillary tube terminus being substantially at the shell terminus;

inserting the direct injection nebulizer into a torch box;

converting the liquid into an aerosol consisting substantially of droplets having a Sauter mean diameter (as determined with respect to normalized volume percent) of less than about 15 micrometers at a point along a centerline of the aerosol at a distance of 15 mm from the terminus of the shell, the droplets further having, at the same point, an axial velocity less than about 80 m/s, a mean velocity of between 12.9 and 37.0 m/s, an axial RMS velocity of between 4.7 and 13.0 m/s, and a radial RMS velocity of between 2.0 and 4.6 rn/s, said converting comprising nebulizing the liquid with the gas by:

(a) outputting gas from the gas output port of the elongate tubular shell without outputting gas from an auxiliary nebulizer gas passageway; and (b) passing the liquid from the sample input port to the sample output port of the capillary tube at a flow rate substantially less than 100 µL/min by (i) drawing the liquid out of the capillary tube without a pump using the Venturi effect caused by said outputting gas from the gas output port or (ii) using a low pressure pump to supplement the Venturi effect such that pressure applied to the liquid is not substantially greater than that provided by a peristaltic pump; and directly injecting the aerosol towards an interaction region of the torch box.

* * * * *